(12) United States Patent
Du et al.

(10) Patent No.: US 9,996,920 B2
(45) Date of Patent: Jun. 12, 2018

(54) AUTOMATED DETECTION AND REPOSITIONING OF MICRO-OBJECTS IN MICROFLUIDIC DEVICES

(71) Applicant: Berkeley Lights, Inc., Emeryville, CA (US)

(72) Inventors: Fenglei Du, Fremont, CA (US); Paul M. Lundquist, San Francisco, CA (US); John A. Tenney, Piedmont, CA (US); Troy A. Lionberger, Berkeley, CA (US)

(73) Assignee: Berkeley Lights, Inc., Emeryville, CA (US)

( * ) Notice: Subject to any disclaimer, the term of this patent is extended or adjusted under 35 U.S.C. 154(b) by 0 days. days.

(21) Appl. No.: 14/963,230

(22) Filed: Dec. 8, 2015

(65) Prior Publication Data

US 2016/0171686 A1 Jun. 16, 2016

Related U.S. Application Data

(60) Provisional application No. 62/259,522, filed on Nov. 24, 2015, provisional application No. 62/089,613, filed on Dec. 9, 2014.

(51) Int. Cl.
*G06T 7/00* (2017.01)
*G01N 15/14* (2006.01)
(Continued)

(52) U.S. Cl.
CPC ....... *G06T 7/0012* (2013.01); *G01N 15/1434* (2013.01); *G01N 15/1463* (2013.01); *G01N 15/1484* (2013.01); *G01N 21/6456* (2013.01);
*G01N 27/453* (2013.01); *G06T 5/50* (2013.01); *B01L 3/502761* (2013.01); *G01N 15/1475* (2013.01); *G01N 2015/0038* (2013.01); *G01N 2015/0065* (2013.01); *G01N 2015/1006* (2013.01); *G01N 2015/1445* (2013.01); *G01N 2015/1486* (2013.01); *G01N 2015/1493* (2013.01); *G01N 2015/1497* (2013.01); *G01N 2021/056* (2013.01);
(Continued)

(58) Field of Classification Search
None
See application file for complete search history.

(56) References Cited

U.S. PATENT DOCUMENTS 5,854,674 A * 12/1998 Lin ..................... G02B 27/46
356/237.1
6,294,063 B1 9/2001 Becker et al.
(Continued)

OTHER PUBLICATIONS

J Chen et al., "Microfluidic approaches for cancer cell detection, characterization, and separation," Lab Chip, 2012, 12, 1753.*
(Continued)

*Primary Examiner* — Matthew Bella
*Assistant Examiner* — Soo Shin
(74) *Attorney, Agent, or Firm* — Kenneth E. Horton; Kirton McConkie

(57) ABSTRACT

Methods are provided for the automated detection of micro-objects in a microfluidic device. In addition, methods are provided for repositioning micro-objects in a microfluidic device. In addition, methods are provided for separating micro-objects in a spatial region of the microfluidic device.

35 Claims, 13 Drawing Sheets

(51) Int. Cl.
  *G06T 5/50* (2006.01)
  *G01N 27/453* (2006.01)
  *G01N 21/64* (2006.01)
  *G01N 15/00* (2006.01)
  *G01N 15/10* (2006.01)
  *G01N 21/05* (2006.01)
  *G01N 21/17* (2006.01)
  *B01L 3/00* (2006.01)

(52) U.S. Cl.
  CPC ........... *G01N 2021/1765* (2013.01); *G01N 2201/0635* (2013.01); *G01N 2201/127* (2013.01); *G06T 2207/30024* (2013.01); *G06T 2207/30101* (2013.01)

(56) References Cited

U.S. PATENT DOCUMENTS

| | | | |
|---|---|---|---|
| 6,916,584 B2* | 7/2005 | Sreenivasan | B29C 35/0888 264/494 |
| 6,942,776 B2 | 9/2005 | Medoro | |
| 7,090,759 B1 | 8/2006 | Seul | |
| 7,842,246 B2* | 11/2010 | Wohlstadter | B01L 3/5085 422/401 |
| 2003/0008364 A1 | 1/2003 | Wang et al. | |
| 2003/0170613 A1* | 9/2003 | Straus | B82Y 20/00 435/5 |
| 2003/0224528 A1 | 12/2003 | Chiou et al. | |
| 2004/0072278 A1 | 4/2004 | Chou et al. | |
| 2004/0191789 A1 | 9/2004 | Manaresi et al. | |
| 2005/0051429 A1* | 3/2005 | Shapiro | B03C 5/024 204/452 |
| 2005/0112548 A1 | 5/2005 | Segawa et al. | |
| 2005/0175981 A1 | 8/2005 | Voldman et al. | |
| 2005/0282175 A1 | 12/2005 | Taylor et al. | |
| 2006/0091015 A1 | 5/2006 | Lau | |
| 2007/0095669 A1 | 5/2007 | Lau et al. | |
| 2008/0013092 A1* | 1/2008 | Maltezos | G01N 21/6452 356/417 |
| 2008/0014575 A1* | 1/2008 | Nelson | G01N 33/54306 435/5 |
| 2008/0182136 A1* | 7/2008 | Arnold | G01N 21/66 429/7 |
| 2008/0302732 A1 | 12/2008 | Soh et al. | |
| 2009/0075828 A1* | 3/2009 | Fisher | C40B 30/04 506/7 |
| 2009/0170186 A1 | 7/2009 | Wu et al. | |
| 2009/0324089 A1* | 12/2009 | Morita | G06T 5/50 382/195 |
| 2010/0003666 A1 | 1/2010 | Lee et al. | |
| 2010/0101960 A1 | 4/2010 | Ohta et al. | |
| 2010/0110177 A1 | 5/2010 | Yamada et al. | |
| 2010/0285490 A1* | 11/2010 | Dees | G01N 33/54373 435/7.1 |
| 2011/0117634 A1 | 5/2011 | Halamish et al. | |
| 2012/0024708 A1 | 2/2012 | Chiou et al. | |
| 2012/0118740 A1 | 5/2012 | Garcia et al. | |
| 2012/0148140 A1* | 6/2012 | Di Carlo | G01N 15/1468 382/133 |
| 2012/0325665 A1 | 12/2012 | Chiou et al. | |
| 2013/0118905 A1 | 5/2013 | Morimoto et al. | |
| 2013/0171628 A1 | 7/2013 | Di Carlo et al. | |
| 2013/0190212 A1 | 7/2013 | Handique et al. | |
| 2013/0204076 A1 | 8/2013 | Han et al. | |
| 2014/0017709 A1* | 1/2014 | Lowe | C12Q 1/001 435/7.92 |
| 2014/0113324 A1* | 4/2014 | Di Carlo | G01N 33/50 435/29 |
| 2014/0116881 A1 | 5/2014 | Chapman et al. | |
| 2014/0376816 A1* | 12/2014 | Lagae | G01N 15/1436 382/195 |
| 2015/0151298 A1 | 6/2015 | Hobbs et al. | |
| 2015/0151307 A1 | 6/2015 | Breinlinger et al. | |
| 2015/0165436 A1 | 6/2015 | Chapman et al. | |
| 2015/0247190 A1* | 9/2015 | Ismagilov | C12Q 1/6851 506/9 |

OTHER PUBLICATIONS

N-T Nguyen et al., "Flow Rate Measurement in Microfluidics Using Optical Sensors," 1$^{st}$ International Conference on Sensing Technology, Nov. 21-23, 2005, Palmerston North, New Zealand.*
IEEE Journal of Solid-state Circuits 38(12):2297-2305 (2003).
Chiou et al., Massively parallel manipulation of single cells and microparticles using optical images, Nature 436:370-73 (2005).
Fuchs, Lab on a Chip 6:121-26 (2006).
Hirano et al., Microfluidic image cytometry for measuring number and sizes of biological cells flowing through a microchannel using the micro-PIV technique; Microfluidic image cytometry, Measurement Science and Technology, IOP, Bristol, GB, vol. 19, No. 2, p. 25402, XP020129404 (2008).
Valley et al., Optoelectronic Tweezers as a Tool for Parallel Single-Cell Manipulation and Stimulation, IEEE Transactions on Biomedical Circuits and Systems 3(6):424-30 (2009).
Lagally et al., Parallel microfluidic arrays for SPRI detection, Proceedings of SPIE, vol. 7759, p. 77590J (2010).
Zhang et al., Controlled Aspiration and Positioning of Biological Cells in a Micropipette, IEEE Transactions on Biomedical Engineering, vol. 59, No. 4, pp. 1032-1040 (2012).
Shin Yong Kyun et al., Automated Microfluidic system for orientation control of mouse embryos, 2013 IEEE/RSJ International Conference on Intelligent Robots and Systems, IEEE. pp. 496-501 (2013).
International Search Report and Written Opinion for PCT Application Serial No. PCT/2015/064575 (dated Jun. 30, 2016), 24 pages.

* cited by examiner

AUTOMATED DETECTION AND REPOSITIONING OF MICRO-OBJECTS IN MICROFLUIDIC DEVICES

CROSS REFERENCE TO RELATED APPLICATION(S)

This application is a non-provisional of, and thus claims the benefit of and/or priority to, U.S. provisional patent application Ser. No. 62/089,613, filed on Dec. 9, 2014 and U.S. provisional patent application Ser. No. 62/259,522, filed on Nov. 24, 2015, the entire contents of which are incorporated herein by reference.

FIELD

The present invention generally relates to methods for detecting the results of an assay within a microfluidic device. In particular, the methods can include steps for automatically selecting specific regions within the microfluidic device for detection of assay results.

BACKGROUND

Efficient and robust detection of micro-objects, such as biological cells or beads, on non-uniform or complicated backgrounds is crucial to the automated manipulation of micro-objects in microfluidic environments. Due to the translucent appearance of certain micro-objects, a non-uniform background that has features similar in size to such micro-objects creates significant detection challenges. Similarly, automated manipulation, such as repositioning cells, is complicated by specific features of OET technology. Some embodiments of the present invention are directed to the robust detection of micro-objects and re-positioning in microfluidic environments.

SUMMARY OF THE INVENTION

In a first aspect, the present invention relates to a method for the automated detection of micro-objects disposed within a microfluidic device. The method comprises capturing a first image of a region in the microfluidic device that may contain a micro-object of interest. The method further comprises inducing movement of fluid within said region. The method further comprises capturing a second image of said region. The method further comprises generating a differential image from the first and second images and identifying a micro-object of interest based on the differential image.

In various embodiments, the region comprises one or more microfluidic device features that are captured in the first and second image, and the differential image does not contain the one or more microfluidic device features. In some embodiments, the one or more microfluidic device features include an array of phototransistors.

In various embodiments, the first and second images are captured using a digital camera or a CCD device.

In various embodiments, inducing movement of said fluid comprises introducing a discrete volume of fluid into said microfluidic device. In some embodiments, the discrete volume of fluid is about 25 pL to about 100 pL.

In various embodiments, the differential image is generated by subtracting said first image from said second image, or vice versa. In some embodiments, the method further comprises determining a first set of light intensity values for one or more pixels corresponding to the first image and a second set of light intensity value for one or more pixels corresponding to the second image and subtracting the first set of light intensity values from the second set of light intensity values, or vice versa, to generate a set of positive-value pixels and a set of negative-value pixels.

In some embodiments, the method further comprises analyzing the set of positive-value pixels to identify one or more sets of pixel clusters, wherein each pixel cluster comprises one or more pixels. The method further comprises determining, for each of the one or more sets of pixel clusters, a feature set comprising information representing one or more of: an area of the set of pixel clusters, a circumference of the set of pixel clusters, a global morphology of the set of pixel clusters, a local morphology of the set of pixel clusters, and a light intensity value associated with the set of pixel clusters. The method further comprises identifying, for each of the one or more sets of pixel clusters, whether the set of pixel clusters corresponds to a micro-object of interest, wherein the identification is based on the determined feature set for the set of pixel clusters.

In various embodiments, the method further comprises detecting pairs of positive-value and negative-value pixels or pixel clusters that differ in their relative position by an amount consistent with said movement of fluid induced in said region and identifying each such pair as representing a current and former location, respectively, of the micro-object of interest.

In a second aspect, the present invention relates a method for the automated detection of micro-objects disposed within a microfluidic device. The method comprises capturing with an imaging device a first image of a region of a microfluidic device that may contain a micro-object of interest. The method further comprises shifting said microfluidic device relative to said imaging device. The method further comprises capturing with said imaging device a second image of the region, wherein said second image is shifted relative to said first image. The method further comprises aligning said first image with said second image. The method further comprises generating a differential image from said first and second images and identifying a micro-object of interest based on the differential image.

In various embodiments, the region comprises one or more microfluidic device features that are captured in the first and second image, and wherein the differential image does not contain the one or more microfluidic device features. In some embodiments, the one or more microfluidic device features include an array of phototransistors.

In various embodiments, the imaging device is a digital camera or a CCD device.

In various embodiments, shifting said microfluidic device comprises moving a stage that is holding said microfluidic device in a direction perpendicular to an optical axis of said imaging device. In some embodiments, the microfluidic device is shifted by about 2 to about 3 microns.

In various embodiments, the first and second images are aligned computationally, and wherein regions of said first and second images that can't be aligned are discarded. In some embodiments, aligning said first and second images comprises aligning circuit elements within the microfluidic device.

In various embodiments, generating a differential image comprises subtracting said first image from said second image, or vice versa. In some embodiments, the method further comprises determining a first set of light intensity values for one or more pixels corresponding to the first image and a second set of light intensity value for one or more pixels corresponding to the second image and subtracting the first set of light intensity values from the second set of light intensity values, or vice versa, to generate a set of positive-value pixels and a set of negative-value pixels.

In some embodiments, the method further comprises analyzing the set of positive-value pixels to identify one or more sets of pixel clusters, wherein each pixel cluster comprises one or more pixels. The method further comprises determining, for each set of pixel clusters of the one or more sets of pixel clusters, a feature set comprising information representing one or more of: an area of the set of pixel clusters, a circumference of the set of pixel clusters, a global morphology of the set of pixel clusters, a local morphology of the set of pixel clusters, and a light intensity value associated with the set of pixel clusters. The method further comprises identifying, for each of the one or more sets of pixel clusters, whether the set of pixel clusters corresponds to a micro-object of interest, wherein the identification is based on the feature set determined for the set of pixel clusters.

In some embodiments, the method further comprises detecting pairs of positive-value and negative-value pixels or pixel clusters that differ in their relative position by an amount consistent with said movement of said microfluidic device relative to said imaging device and identifying each such pair as representing a current and former location, respectively, of the micro-object of interest.

In a third aspect, the present invention provides a method for the automated detection of micro-objects disposed within a microfluidic device. The method comprises capturing an image of a region in the microfluidic device that may contain a micro-object of interest. The method further comprises determining periodic structures in the image using a Fourier transform. The method further comprises generating a filtered image by removing the period structures from the image and identifying a micro-object of interest based on the filtered image.

In various embodiments, the periodic structures correspond to one or more microfluidic device features. In some embodiments, the one or more microfluidic device features include an array of phototransistors.

In various embodiments, the method further comprises determining a set of light intensity values for one or more pixels corresponding to the filtered image and generating a set of positive-value pixels based on the filtered image.

In various embodiments, the method further comprises analyzing the set of positive-value pixels to identify one or more sets of pixel clusters, wherein each pixel cluster comprises one or more pixels. The method further comprises determining, for each of the one or more sets of pixels clusters, a feature set comprising information representing one or more of: an area of the set of pixel clusters, a circumference of the set of pixel clusters, a global morphology of the set of pixel clusters, a local morphology of the set of pixel clusters and a light intensity value associated with the set of pixel clusters. The method further comprises identifying, for each of the one or more sets of pixel clusters, whether the set of pixel clusters corresponds to the micro-object of interest, wherein the identification is based on the feature set determined for the set of pixel clusters.

In a fourth aspect, the present invention provides a method of re-positioning micro-objects in a microfluidic device comprising a set of sequestration pens. The method comprises identifying a set of micro-objects disposed within the microfluidic device. The method further comprises computing one or more trajectories, wherein each trajectory is a path that connects one micro-object of the set of micro-objects with one sequestration pen of the set of sequestration pens. The method further comprises selecting, for one or more micro-objects of the set of micro-objects, a trajectory of the one or more trajectories. The method further comprises re-positioning at least one micro-object of the one or more micro-objects of the set of micro-objects by moving the micro-object along its selected trajectory.

In various embodiments, the re-positioning at least one micro-object of the one or more micro-objects of the set of micro-objects comprises moving at least a first micro-object along its selected trajectory and a second micro-object along its selected trajectory. In some embodiments, the first and second micro-objects are moved in parallel.

In various embodiments, the method further comprises computing a density value associated with the set of micro-objects and computing the one or more trajectories based, at least in part, on the density value associated with the set of micro-objects. In some embodiments, the method further comprises determining that the density value exceeds a threshold value and computing, for at least one micro-object of the set of micro-objects, one or more trajectories connecting the micro-object with one or more sequestration pens of the set of sequestration pens. In some embodiments, the method further comprises determining that the density value does not exceed a threshold value and computing, for at least one sequestration pen of the set of sequestration pens, one or more trajectories connecting the sequestration pen with one or more micro-objects of the set of micro-objects.

In various embodiments, the method further comprises identifying the set of sequestration pens. In some embodiments, identifying the set of sequestration pens comprises identifying empty sequestration pens amongst a plurality of sequestration pens.

In various embodiments, selecting a trajectory of the one or more trajectories comprises selecting a trajectory for each micro-object that is being repositioned such that the sum of the lengths of the selected trajectories is minimized. In some embodiments, minimizing the sum of the lengths of the selected trajectories comprises using at least one of the following: a greedy algorithm, a heuristics-based algorithm, a non-linear algorithm, and a constrained search.

In various embodiments, selecting a trajectory of the one or more trajectories further comprises determining whether the trajectory exceeds a pre-determined maximum length.

In some embodiments, re-positioning at least one micro-object of the one or more micro-objects comprises accelerating each of the at least one micro-objects from an initial velocity to a traveling velocity over a first time period. In some embodiments, re-positioning at least one micro-object of the one or more micro-objects comprises decelerating each of the at least one micro-objects from the traveling velocity to a final velocity over a second time period.

In a fifth aspect, the present invention relates to a method of re-positioning micro-objects in a microfluidic device. The method comprises identifying a set of micro-objects disposed within a specified spatial region of the microfluidic device. The method further comprises calculating a set of vertices that divide the specified spatial region into sub-regions, each of which contains one or more micro-object(s) of the set of micro-objects. The method further comprises generating a modified first light cage for at least one micro-object of the set of micro-objects based on the calculated set of vertices; and moving the modified light cage relative to the specified spatial region of the microfluidic device to re-position the at least one micro-object.

In various embodiments, the method further comprises computing, for a first micro-object of the set of micro-objects, a first light cage. The method further comprises computing the intersection between the first light cage and the set of vertices. The method further comprises generating the modified first light cage based on the intersection between the first light cage and the set of vertices.

In various embodiments, the method further comprises calculating a set of vertices that maximize the distance between a subset of the calculated set of vertices that are adjacent to each micro-object of the set of micro-objects and the micro-object.

In various embodiments, the method further comprises calculating a set of vertices that divide the specified spatial region into sub-regions, wherein at least a subset of the sub-regions contains a single micro-object of the set of micro-objects.

In various embodiments, the method further comprises calculating a Delaunay triangulation of the set of micro-objects. The method further comprises generating a Voronoi diagram based on the Delaunay triangulation of the set of micro-objects and identifying the set of vertices based on the Voronoi diagram.

In various embodiments, the method further comprises computing, for a second micro-object of the set of micro-objects, a second light cage. The method further comprises computing the intersection between the second light cage and the set of vertices and generating a modified second light cage based on the intersection between the second light cage and the set of vertices, wherein the modified second light cage does not intersect with the modified first light cage.

In various embodiments, the method further comprises moving both the first modified light cage and the second modified light cage relative to the specified spatial region of the microfluidic device to physically separate the first micro-object and the second micro-object. In some embodiments, the first micro-object and the second micro-object are initially located in adjacent sub-regions of the specified spatial region.

In various embodiments, the set of micro-objects is identified according to the methods described above with respect to the first aspect, second aspect and third aspect of the present invention.

In a sixth aspect, the present invention relates to a machine readable storage device for storing non-transitory machine readable instructions for carrying out the method of the first aspect of the present invention. In a seventh aspect, the present invention relates to a machine readable storage device for storing non-transitory machine readable instructions for carrying out the method of the second aspect of the present invention. In an eighth aspect, the present invention relates to a machine readable storage device for storing non-transitory machine readable instructions for carrying out the method of the third aspect of the present invention. In a ninth aspect, the present invention relates to a machine readable storage device for storing non-transitory machine readable instructions for carrying out the method of the fourth aspect of the present invention. In an tenth aspect, the present invention relates to a machine readable storage device for storing non-transitory machine readable instructions for carrying out the method of the fifth aspect of the present invention.

In various embodiments and aspects of the present invention, the micro-object of interest is a cell. In various embodiments and aspects of the present invention, the cell is a mammalian cell. In various embodiments and aspects of the present invention, the cell is selected from the group consisting of a blood cell, a hybridoma, a cancer cell, and a transformed cell.

DETAILED DESCRIPTION OF EXEMPLARY EMBODIMENTS

Figure 1:
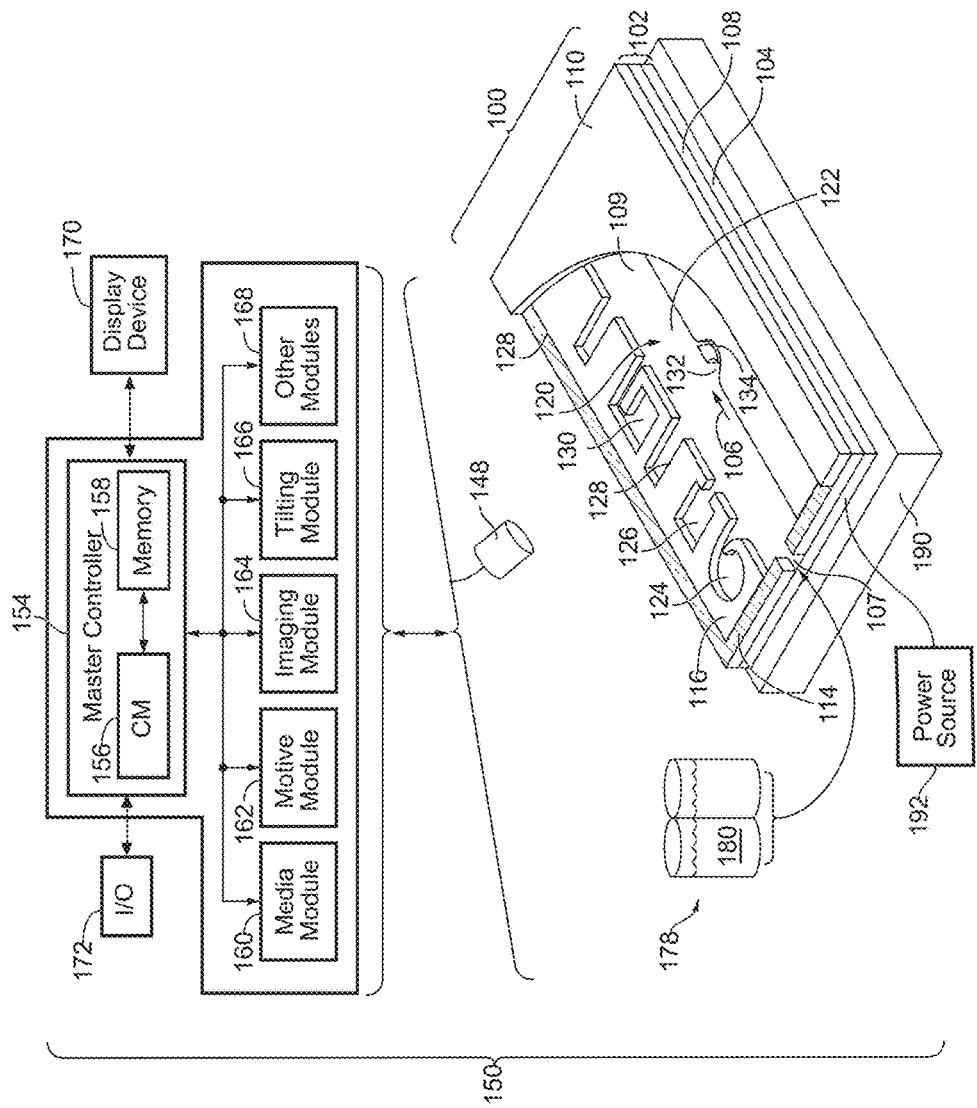
FIG. 1 illustrates an example of a system for use with a microfluidic device and associated control equipment according to some embodiments of the invention.

This specification describes exemplary embodiments and applications of the invention. The invention, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. In addition, where reference is made to a list of elements (e.g., elements a, b, c), such reference is intended to include any one of the listed elements by itself, any combination of less than all of the listed elements, and/or a combination of all of the listed elements.

Section divisions in the specification are for ease of review only and do not limit any combination of elements discussed.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

As used herein, the term "ones" means more than one. As used herein, the term "plurality" can be 2, 3, 4, 5, 6, 7, 8, 9, 10, or more.

As used herein, the term "disposed" encompasses within its meaning "located."

As used herein, a "microfluidic device" or "microfluidic apparatus" is a device that includes one or more discrete microfluidic circuits configured to hold a fluid, each microfluidic circuit comprised of fluidically interconnected circuit elements, including but not limited to region(s), flow path(s), channel(s), chamber(s), and/or pen(s), and at least two ports configured to allow the fluid (and, optionally, micro-objects suspended in the fluid) to flow into and/or out of the microfluidic device. Typically, a microfluidic circuit of a microfluidic device will include at least one microfluidic channel and at least one chamber, and will hold a volume of fluid of less than about 1 mL, e.g., less than about 750, 500, 250, 200, 150, 100, 75, 50, 25, 20, 15, 10, 9, 8, 7, 6, 5, 4, 3, or 2 µL. In certain embodiments, the microfluidic circuit holds about 1-2, 1-3, 1-4, 1-5, 2-5, 2-8, 2-10, 2-12, 2-15, 2-20, 5-20, 5-30, 5-40, 5-50, 10-50, 10-75, 10-100, 20-100, 20-150, 20-200, 50-200, 50-250, or 50-300 µL.

As used herein, a "nanofluidic device" or "nanofluidic apparatus" is a type of microfluidic device having a microfluidic circuit that contains at least one circuit element configured to hold a volume of fluid of less than about 1 µL, e.g., less than about 750, 500, 250, 200, 150, 100, 75, 50, 25, 20, 15, 10, 9, 8, 7, 6, 5, 4, 3, 2, 1 nL or less. Typically, a nanofluidic device will comprise a plurality of circuit elements (e.g., at least 2, 3, 4, 5, 6, 7, 8, 9, 10, 15, 20, 25, 50, 75, 100, 150, 200, 250, 300, 400, 500, 600, 700, 800, 900, 1000, 1500, 2000, 2500, 3000, 3500, 4000, 4500, 5000, 6000, 7000, 8000, 9000, 10,000, or more). In certain embodiments, one or more (e.g., all) of the at least one circuit elements is configured to hold a volume of fluid of about 100 pL to 1 nL, 100 pL to 2 nL, 100 pL to 5 nL, 250 pL to 2 nL, 250 pL to 5 nL, 250 pL to 10 nL, 500 pL to 5 nL, 500 pL to 10 nL, 500 pL to 15 nL, 750 pL to 10 nL, 750 pL to 15 nL, 750 pL to 20 nL, 1 to 10 nL, 1 to 15 nL, 1 to 20 nL, 1 to 25 nL, or 1 to 50 nL. In other embodiments, one or more (e.g., all) of the at least one circuit elements is configured to hold a volume of fluid of about 100 to 200 nL, 100 to 300 nL, 100 to 400 nL, 100 to 500 nL, 200 to 300 nL, 200 to 400 nL, 200 to 500 nL, 200 to 600 nL, 200 to 700 nL, 250 to 400 nL, 250 to 500 nL, 250 to 600 nL, or 250 to 750 nL.

A "microfluidic channel" or "flow channel" as used herein refers to flow region of a microfluidic device having a length that is significantly longer than both the horizontal and vertical dimensions. For example, the flow channel can be at least 5 times the length of either the horizontal or vertical dimension, e.g., at least 10 times the length, at least 25 times the length, at least 100 times the length, at least 200 times the length, at least 500 times the length, at least 1,000 times the length, at least 5,000 times the length, or longer. In some embodiments, the length of a flow channel is in the range of from about 100,000 microns to about 500,000 microns, including any range therebetween. In some embodiments, the horizontal dimension is in the range of from about 100 microns to about 1000 microns (e.g., about 150 to about 500 microns) and the vertical dimension is in the range of from about 25 microns to about 200 microns, e.g., from about 40 to about 150 microns. It is noted that a flow channel may have a variety of different spatial configurations in a microfluidic device, and thus is not restricted to a perfectly linear element. For example, a flow channel may be, or include one or more sections having, the following configurations: curve, bend, spiral, incline, decline, fork (e.g., multiple different flow paths), and any combination thereof. In addition, a flow channel may have different cross-sectional areas along its path, widening and constricting to provide a desired fluid flow therein.

As used herein, the term "obstruction" refers generally to a bump or similar type of structure that is sufficiently large so as to partially (but not completely) impede movement of target micro-objects between two different regions or circuit elements in a microfluidic device. The two different regions/circuit elements can be, for example, a microfluidic sequestration pen and a microfluidic channel, or a connection region and an isolation region of a microfluidic sequestration pen.

As used herein, the term "constriction" refers generally to a narrowing of a width of a circuit element (or an interface between two circuit elements) in a microfluidic device. The constriction can be located, for example, at the interface between a microfluidic sequestration pen and a microfluidic channel, or at the interface between an isolation region and a connection region of a microfluidic sequestration pen.

As used herein, the term "transparent" refers to a material which allows visible light to pass through without substantially altering the light as is passes through.

As used herein, the term "micro-object" refers generally to any microscopic object that may be isolated and collected in accordance with the present invention. Non-limiting examples of micro-objects include: inanimate micro-objects such as microparticles; microbeads (e.g., polystyrene beads, Luminex™ beads, or the like); magnetic beads; microrods; microwires; quantum dots, and the like; biological micro-objects such as cells (e.g., embryos, oocytes, sperm cells, cells dissociated from a tissue, eukaryotic cells, protist cells, animal cells, mammalian cells, human cells, immunological cells, hybridomas, cultured cells, cells from a cell line, cancer cells, infected cells, transfected and/or transformed cells, reporter cells, prokaryotic cell, and the like); biological organelles; vesicles, or complexes; synthetic vesicles; liposomes (e.g., synthetic or derived from membrane preparations); lipid nanorafts (as described in Ritchie et al. (2009) "Reconstitution of Membrane Proteins in Phospholipid Bilayer Nanodiscs," Methods Enzymol., 464:211-231), and the like; or a combination of inanimate micro-objects and biological micro-objects (e.g., microbeads attached to cells, liposome-coated micro-beads, liposome-coated magnetic beads, or the like). Beads may further have other moieties/molecules covalently or non-covalently attached, such as fluorescent labels, proteins, small molecule signaling moieties, antigens, or chemical/biological species capable of use in an assay.

As used herein, the term "maintaining (a) cell(s)" refers to providing an environment comprising both fluidic and gaseous components and, optionally a surface, that provides the conditions necessary to keep the cells viable and/or expanding.

A "component" of a fluidic medium is any chemical or biochemical molecule present in the medium, including solvent molecules, ions, small molecules, antibiotics, nucleotides and nucleosides, nucleic acids, amino acids, peptides, proteins, sugars, carbohydrates, lipids, fatty acids, cholesterol, metabolites, or the like.

As used herein in reference to a fluidic medium, "diffuse" and "diffusion" refer to thermodynamic movement of a component of the fluidic medium down a concentration gradient.

The phrase "flow of a medium" means bulk movement of a fluidic medium primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase "substantially no flow" refers to a rate of flow of a fluidic medium that, averaged over time, is less than the rate of diffusion of components of a material (e.g., an analyte of interest) into or within the fluidic medium. The rate of diffusion of components of such a material can depend on, for example, temperature, the size of the components, and the strength of interactions between the components and the fluidic medium.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the device.

A microfluidic (or nanofluidic) device can comprise "swept" regions and "unswept" regions. As used herein, a "swept" region is comprised of one or more fluidically interconnected circuit elements of a microfluidic circuit, each of which experiences a flow of medium when fluid is flowing through the microfluidic circuit. The circuit elements of a swept region can include, for example, regions, channels, and all or parts of chambers. As used herein, an "unswept" region is comprised of one or more fluidically interconnected circuit element of a microfluidic circuit, each of which experiences substantially no flux of fluid when fluid is flowing through the microfluidic circuit. An unswept region can be fluidically connected to a swept region, provided the fluidic connections are structured to enable diffusion but substantially no flow of media between the swept region and the unswept region. The microfluidic device can thus be structured to substantially isolate an unswept region from a flow of medium in a swept region, while enabling substantially only diffusive fluidic communication between the swept region and the unswept region. For example, a flow channel of a micro-fluidic device is an example of a swept region while an isolation region (described in further detail below) of a microfluidic device is an example of an unswept region.

As used herein, a "flow path" refers to one or more fluidically connected circuit elements (e.g. channel(s), region(s), chamber(s) and the like) that define, and are subject to, the trajectory of a flow of medium. A flow path is thus an example of a swept region of a microfluidic device. Other circuit elements (e.g., unswept regions) may be fluidically connected with the circuit elements that comprise the flow path without being subject to the flow of medium in the flow path.

The capability of biological micro-objects (e.g., biological cells) to produce specific biological materials (e.g., proteins, such as antibodies) can be assayed in such a microfluidic device. In a specific embodiment of an assay, sample material comprising biological micro-objects (e.g., cells) to be assayed for production of an analyte of interest can be loaded into a swept region of the microfluidic device. Ones of the biological micro-objects (e.g., mammalian cells, such as human cells) can be selected for particular characteristics and disposed in unswept regions. The remaining sample material can then be flowed out of the swept region and an assay material flowed into the swept region. Because the selected biological micro-objects are in unswept regions, the selected biological micro-objects are not substantially affected by the flowing out of the remaining sample material or the flowing in of the assay material. The selected biological micro-objects can be allowed to produce the analyte of interest, which can diffuse from the unswept regions into the swept region, where the analyte of interest can react with the assay material to produce localized detectable reactions, each of which can be correlated to a particular unswept region. Any unswept region associated with a detected reaction can be analyzed to determine which, if any, of the biological micro-objects in the unswept region are sufficient producers of the analyte of interest.

Microfluidic Devices and Systems for Operating and Observing Such Devices.

FIG. 1 illustrates an example of a microfluidic device 100 and a system 150 which can be used in the practice of the present invention. A perspective view of the microfluidic device 100 is shown having a partial cut-away of its cover 110 to provide a partial view into the microfluidic device 100. The microfluidic device 100 generally comprises a microfluidic circuit 120 comprising a flow path 106 through which a fluidic medium 180 can flow, optionally carrying one or more micro-objects (not shown) into and/or through the microfluidic circuit 120. Although a single microfluidic circuit 120 is illustrated in FIG. 1, suitable microfluidic devices can include a plurality (e.g., 2 or 3) of such microfluidic circuits. Regardless, the microfluidic device 100 can be configured to be a nanofluidic device. In the embodiment illustrated in FIG. 1, the microfluidic circuit 120 comprises a plurality of microfluidic sequestration pens 124, 126, 128, and 130, each having one or more openings in fluidic communication with flow path 106. As discussed further below, the microfluidic sequestration pens comprise various features and structures that have been optimized for retaining micro-objects in the microfluidic device, such as microfluidic device 100, even when a medium 180 is flowing through the flow path 106. Before turning to the foregoing, however, a brief description of microfluidic device 100 and system 150 is provided.

As generally illustrated in FIG. 1, the microfluidic circuit 120 is defined by an enclosure 102. Although the enclosure 102 can be physically structured in different configurations, in the example shown in FIG. 1 the enclosure 102 is depicted as comprising a support structure 104 (e.g., a base), a microfluidic circuit structure 108, and a cover 110. The support structure 104, microfluidic circuit structure 108, and cover 110 can be attached to each other. For example, the microfluidic circuit structure 108 can be disposed on an inner surface 109 of the support structure 104, and the cover 110 can be disposed over the microfluidic circuit structure 108. Together with the support structure 104 and cover 110, the microfluidic circuit structure 108 can define the elements of the microfluidic circuit 120.

The support structure 104 can be at the bottom and the cover 110 at the top of the microfluidic circuit 120 as illustrated in FIG. 1. Alternatively, the support structure 104 and the cover 110 can be configured in other orientations.

For example, the support structure 104 can be at the top and the cover 110 at the bottom of the microfluidic circuit 120. Regardless, there can be one or more ports 107 each comprising a passage into or out of the enclosure 102. Examples of a passage include a valve, a gate, a pass-through hole, or the like. As illustrated, port 107 is a pass-through hole created by a gap in the microfluidic circuit structure 108. However, the port 107 can be situated in other components of the enclosure 102, such as the cover 110. Only one port 107 is illustrated in FIG. 1 but the microfluidic circuit 120 can have two or more ports 107. For example, there can be a first port 107 that functions as an inlet for fluid entering the microfluidic circuit 120, and there can be a second port 107 that functions as an outlet for fluid exiting the microfluidic circuit 120. Whether a port 107 function as an inlet or an outlet can depend upon the direction that fluid flows through flow path 106.

The support structure 104 can comprise one or more electrodes (not shown) and a substrate or a plurality of interconnected substrates. For example, the support structure 104 can comprise one or more semiconductor substrates, each of which is electrically connected to an electrode (e.g., all or a subset of the semiconductor substrates can be electrically connected to a single electrode). The support structure 104 can further comprise a printed circuit board assembly ("PCBA"). For example, the semiconductor substrate(s) can be mounted on a PCBA.

The microfluidic circuit structure 108 can define circuit elements of the microfluidic circuit 120. Such circuit elements can comprise spaces or regions that can be fluidly interconnected when microfluidic circuit 120 is filled with fluid, such as flow channels, chambers, pens, traps, and the like. In the microfluidic circuit 120 illustrated in FIG. 1, the microfluidic circuit structure 108 comprises a frame 114 and a microfluidic circuit material 116. The frame 114 can partially or completely enclose the microfluidic circuit material 116. The frame 114 can be, for example, a relatively rigid structure substantially surrounding the microfluidic circuit material 116. For example the frame 114 can comprise a metal material.

The microfluidic circuit material 116 can be patterned with cavities or the like to define circuit elements and interconnections of the microfluidic circuit 120. The microfluidic circuit material 116 can comprise a flexible material, such as a flexible polymer (e.g. rubber, plastic, elastomer, silicone, polydimethylsiloxane ("PDMS"), or the like), which can be gas permeable. Other examples of materials that can compose microfluidic circuit material 116 include molded glass, an etchable material such as silicone (e.g. photo-patternable silicone or "PPS"), photo-resist (e.g., SU8), or the like. In some embodiments, such materials—and thus the microfluidic circuit material 116—can be rigid and/or substantially impermeable to gas. Regardless, microfluidic circuit material 116 can be disposed on the support structure 104 and inside the frame 114.

The cover 110 can be an integral part of the frame 114 and/or the microfluidic circuit material 116. Alternatively, the cover 110 can be a structurally distinct element, as illustrated in FIG. 1. The cover 110 can comprise the same or different materials than the frame 114 and/or the microfluidic circuit material 116. Similarly, the support structure 104 can be a separate structure from the frame 114 or microfluidic circuit material 116 as illustrated, or an integral part of the frame 114 or microfluidic circuit material 116. Likewise the frame 114 and microfluidic circuit material 116 can be separate structures as shown in FIG. 1 or integral portions of the same structure.

In some embodiments, the cover 110 can comprise a rigid material. The rigid material may be glass or a material with similar properties. In some embodiments, the cover 110 can comprise a deformable material. The deformable material can be a polymer, such as PDMS. In some embodiments, the cover 110 can comprise both rigid and deformable materials. For example, one or more portions of cover 110 (e.g., one or more portions positioned over sequestration pens 124, 126, 128, 130) can comprise a deformable material that interfaces with rigid materials of the cover 110. In some embodiments, the cover 110 can further include one or more electrodes. The one or more electrodes can comprise a conductive oxide, such as indium-tin-oxide (ITO), which may be coated on glass or a similarly insulating material. Alternatively, the one or more electrodes can be flexible electrodes, such as single-walled nanotubes, multi-walled nanotubes, nanowires, clusters of electrically conductive nanoparticles, or combinations thereof, embedded in a deformable material, such as a polymer (e.g., PDMS). Flexible electrodes that can be used in microfluidic devices have been described, for example, in U.S. 2012/0325665 (Chiou et al.), the contents of which are incorporated herein by reference. In some embodiments, the cover 110 can be modified (e.g., by conditioning all or part of a surface that faces inward toward the microfluidic circuit 120) to support cell adhesion, viability and/or growth. The modification may include a coating of a synthetic or natural polymer. In some embodiments, the cover 110 and/or the support structure 104 can be transparent to light. The cover 110 may also include at least one material that is gas permeable (e.g., PDMS or PPS).

FIG. 1 also shows a system 150 for operating and controlling microfluidic devices, such as microfluidic device 100. System 150, as illustrated, includes an electrical power source 192, an imaging device 194, and a tilting device 190.

The electrical power source 192 can provide electric power to the microfluidic device 100 and/or tilting device 190, providing biasing voltages or currents as needed. The electrical power source 192 can, for example, comprise one or more alternating current (AC) and/or direct current (DC) voltage or current sources. The imaging device 194 can comprise a device, such as a digital camera, for capturing images inside microfluidic circuit 120. In some instances, the imaging device 194 further comprises a detector having a fast frame rate and/or high sensitivity (e.g. for low light applications). The imaging device 194 can also include a mechanism for directing stimulating radiation and/or light beams into the microfluidic circuit 120 and collecting radiation and/or light beams reflected or emitted from the microfluidic circuit 120 (or micro-objects contained therein). The emitted light beams may be in the visible spectrum and may, e.g., include fluorescent emissions. The reflected light beams may include reflected emissions originating from an LED or a wide spectrum lamp, such as a mercury lamp (e.g. a high pressure mercury lamp) or a Xenon arc lamp. As discussed with respect to FIG. 3, the imaging device 194 may further include a microscope (or an optical train), which may or may not include an eyepiece.

System 150 further comprises a tilting device 190 configured to rotate a microfluidic device 100 about one or more axes of rotation. In some embodiments, the tilting device 190 is configured to support and/or hold the enclosure 102 comprising the microfluidic circuit 120 about at least one axis such that the microfluidic device 100 (and thus the microfluidic circuit 120) can be held in a level orientation (i.e. at 0° relative to x- and y-axes), a vertical orientation (i.e. at 90° relative to the x-axis and/or the y-axis), or any orientation therebetween. The orientation of the microfluidic device 100 (and the microfluidic circuit 120) relative to an axis is referred to herein as the "tilt" of the microfluidic device 100 (and the microfluidic circuit 120). For example, the tilting device 190 can tilt the microfluidic device 100 at 0.1°, 0.2°, 0.3°, 0.4°, 0.5°, 0.6°, 0.7°, 0.8°, 0.9°, 1°, 2°, 3°, 4°, 5°, 10°, 15°, 20°, 25°, 30°, 35°, 40°, 45°, 50°, 55°, 60°, 65°, 70°, 75°, 80°, 90° relative to the x-axis or any degree therebetween. The level orientation (and thus the x- and y-axes) is defined as normal to a vertical axis defined by the force of gravity. The tilting device can also tilt the microfluidic device 100 (and the microfluidic circuit 120) to any degree greater than 90° relative to the x-axis and/or y-axis, or tilt the microfluidic device 100 (and the microfluidic circuit 120) 180° relative to the x-axis or the y-axis in order to fully invert the microfluidic device 100 (and the microfluidic circuit 120). Similarly, in some embodiments, the tilting device 190 tilts the microfluidic device 100 (and the microfluidic circuit 120) about an axis of rotation defined by flow path 106 or some other portion of microfluidic circuit 120.

In some instances, the microfluidic device 100 is tilted into a vertical orientation such that the flow path 106 is positioned above or below one or more sequestration pens. The term "above" as used herein denotes that the flow path 106 is positioned higher than the one or more sequestration pens on a vertical axis defined by the force of gravity (i.e. an object in a sequestration pen above a flow path 106 would have a higher gravitational potential energy than an object in the flow path). The term "below" as used herein denotes that the flow path 106 is positioned lower than the one or more sequestration pens on a vertical axis defined by the force of gravity (i.e. an object in a sequestration pen below a flow path 106 would have a lower gravitational potential energy than an object in the flow path).

In some instances, the tilting device 190 tilts the microfluidic device 100 about an axis that is parallel to the flow path 106. Moreover, the microfluidic device 100 can be tilted to an angle of less than 90° such that the flow path 106 is located above or below one or more sequestration pens without being located directly above or below the sequestration pens. In other instances, the tilting device 190 tilts the microfluidic device 100 about an axis perpendicular to the flow path 106. In still other instances, the tilting device 190 tilts the microfluidic device 100 about an axis that is neither parallel nor perpendicular to the flow path 106.

System 150 can further include a media source 178. The media source 178 (e.g., a container, reservoir, or the like) can comprise multiple sections or containers, each for holding a different fluidic medium 180. Thus, the media source 178 can be a device that is outside of and separate from the microfluidic device 100, as illustrated in FIG. 1. Alternatively, the media source 178 can be located in whole or in part inside the enclosure 102 of the microfluidic device 100. For example, the media source 178 can comprise reservoirs that are part of the microfluidic device 100.

FIG. 1 also illustrates simplified block diagram depictions of examples of control and monitoring equipment 152 that constitute part of system 150 and can be utilized in conjunction with a microfluidic device 100. As shown, examples of such control and monitoring equipment 152 include a master controller 154 comprising a media module 160 for controlling the media source 178, a motive module 162 for controlling movement and/or selection of micro-objects (not shown) and/or medium (e.g., droplets of medium) in the microfluidic circuit 120, an imaging module 164 for controlling an imaging device 194 (e.g., a camera, microscope, light source or any combination thereof) for capturing images (e.g., digital images), and a tilting module 166 for controlling a tilting device 190. The control equipment 152 can also include other modules 168 for controlling, monitoring, or performing other functions with respect to the microfluidic device 100. As shown, the equipment 152 can further include a display device 170 and an input/output device 172.

The master controller 154 can comprise a control module 156 and a digital memory 158. The control module 156 can comprise, for example, a digital processor configured to operate in accordance with machine executable instructions (e.g., software, firmware, source code, or the like) stored as non-transitory data or signals in the memory 158. Alternatively or in addition, the control module 156 can comprise hardwired digital circuitry and/or analog circuitry. The media module 160, motive module 162, imaging module 164, tilting module 166, and/or other modules 168 can be similarly configured. Thus, functions, processes acts, actions, or steps of a process discussed herein as being performed with respect to the microfluidic device 100 or any other microfluidic apparatus can be performed by any one or more of the master controller 154, media module 160, motive module 162, imaging module 164, tilting module 166, and/or other modules 168 configured as discussed above. Similarly, the master controller 154, media module 160, motive module 162, imaging module 164, tilting module 166, and/or other modules 168 may be communicatively coupled to transmit and receive data used in any function, process, act, action or step discussed herein.

The media module 160 controls the media source 178. For example, the media module 160 can control the media source 178 to input a selected fluidic medium 180 into the enclosure 102 (e.g., through an inlet port 107). The media module 160 can also control removal of media from the enclosure 102 (e.g., through an outlet port (not shown)). One or more media can thus be selectively input into and removed from the microfluidic circuit 120. The media module 160 can also control the flow of fluidic medium 180 in the flow path 106 inside the microfluidic circuit 120. For example, in some embodiments media module 160 stops the flow of media 180 in the flow path 106 and through the enclosure 102 prior to the tilting module 166 causing the tilting device 190 to tilt the microfluidic device 100 to a desired angle of incline.

The motive module 162 can be configured to control selection, trapping, and movement of micro-objects (not shown) in the microfluidic circuit 120. As discussed below with respect to FIGS. 2A and 2B, the enclosure 102 can comprise a dielectrophoresis (DEP), optoelectronic tweezers (OET) and/or opto-electrowetting (OEW) configuration (not shown in FIG. 1), and the motive module 162 can control the activation of electrodes and/or transistors (e.g., phototransistors) to select and move micro-objects (not shown) and/or droplets of medium (not shown) in the flow path 106 and/or sequestration pens 124, 126, 128, 130.

The imaging module 164 can control the imaging device 194. For example, the imaging module 164 can receive and process image data from the imaging device 194. Image data from the imaging device 194 can comprise any type of information captured by the imaging device 194 (e.g., the presence or absence of micro-objects, droplets of medium, accumulation of label, such as fluorescent label, etc.). Using the information captured by the imaging device 194, the imaging module 164 can further calculate the position of objects (e.g., micro-objects, droplets of medium) and/or the rate of motion of such objects within the microfluidic device 100.

The tilting module 166 can control the tilting motions of tilting device 190. Alternatively or in addition, the tilting module 166 can control the tilting rate and timing to optimize transfer of micro-objects to the one or more sequestration pens via gravitational forces. The tilting module 166 is communicatively coupled with the imaging module 164 to receive data describing the motion of micro-objects and/or droplets of medium in the microfluidic circuit 120. Using this data, the tilting module 166 may adjust the tilt of the microfluidic circuit 120 in order to adjust the rate at which micro-objects and/or droplets of medium move in the microfluidic circuit 120. The tilting module 166 may also use this data to iteratively adjust the position of a micro-object and/or droplet of medium in the microfluidic circuit 120.

In the example shown in FIG. 1, the microfluidic circuit 120 is illustrated as comprising a microfluidic channel 122 and sequestration pens 124, 126, 128, 130. Each pen comprises an opening to channel 122, but otherwise is enclosed such that the pens can substantially isolate micro-objects inside the pen from fluidic medium 180 and/or micro-objects in the flow path 106 of channel 122 or in other pens. In some instances, pens 124, 126, 128, 130 are configured to physically corral one or more micro-objects within the microfluidic circuit 120. Sequestration pens in accordance with the present invention can comprise various shapes, surfaces and features that are optimized for use with DEP, OET, OEW, and/or gravitational forces, as will be discussed and shown in detail below.

The microfluidic circuit 120 may comprise any number of microfluidic sequestration pens. Although five sequestration pens are shown, microfluidic circuit 120 may have fewer or more sequestration pens. As shown, microfluidic sequestration pens 124, 126, 128, and 130 of microfluidic circuit 120 each comprise differing features and shapes which may provide one or more benefits useful in performing assays (e.g. culturing and retaining micro-objects used in assays). In some embodiments, the microfluidic circuit 120 comprises a plurality of identical microfluidic sequestration pens. In some embodiments, the microfluidic circuit 120 comprises a plurality of microfluidic sequestration pens, wherein two or more of the sequestration pens comprise differing structures and/or features. For example, the sequestration pens can provide differing benefits with regard to performing assays.

In the embodiment illustrated in FIG. 1, a single channel 122 and flow path 106 is shown. However, other embodiments may contain multiple channels 122, each configured to comprise a flow path 106. The microfluidic circuit 120 further comprises an inlet valve or port 107 in fluid communication with the flow path 106 and fluidic medium 180, whereby fluidic medium 180 can access channel 122 via the inlet port 107. In some instances, the flow path 106 comprises a single path. In some instances, the single path is arranged in a zigzag pattern whereby the flow path 106 travels across the microfluidic device 100 two or more times in alternating directions.

In some instances, microfluidic circuit 120 comprises a plurality of parallel channels 122 and flow paths 106, wherein the fluidic medium 180 within each flow path 106 flows in the same direction. In some instances, the fluidic medium within each flow path 106 flows in at least one of a forward or reverse direction. In some instances, a plurality of sequestration pens are configured (e.g., relative to a channel 122) such that they can be loaded with target micro-objects in parallel.

In some embodiments, microfluidic circuit 120 further comprises one or more micro-object traps 132. The traps 132 are generally formed in a wall forming the boundary of a channel 122, and may be positioned opposite an opening of one or more of the microfluidic sequestration pens 124, 126, 128, 130. In some embodiments, the traps 132 are configured to receive or capture a single micro-object from the flow path 106. In some embodiments, the traps 132 are configured to receive or capture a plurality of micro-objects from the flow path 106. In some instances, the traps 132 comprise a volume approximately equal to the volume of a single target micro-object.

The traps 132 may further comprise an opening which is configured to assist the flow of targeted micro-objects into the traps 132. In some instances, the traps 132 comprise an opening having a height and width that is approximately equal to the dimensions of a single target micro-object, whereby larger micro-objects are prevented from entering into the micro-object trap. The traps 132 may further comprise other features configured to assist in retention of targeted micro-objects within the trap 132. In some instances, the trap 132 is aligned with and situated on the opposite side of a channel 122 relative to the opening of a microfluidic sequestration pen, such that upon tilting the microfluidic device 100 about an axis parallel to the channel 122, the trapped micro-object exits the trap 132 at a trajectory that causes the micro-object to fall into the opening of the sequestration pen. In some instances, the trap 132 comprises a side passage 134 that is smaller than the target micro-object in order to facilitate flow through the trap 132 and thereby increase the likelihood of capturing a micro-object in the trap 132.

In some embodiments, dielectrophoretic (DEP) forces are applied across the fluidic medium 180 (e.g., in the flow path and/or in the sequestration pens) via one or more electrodes (not shown) to manipulate, transport, separate and sort micro-objects located therein. For example, in some embodiments, DEP forces are applied to one or more portions of microfluidic circuit 120 in order to transfer a single micro-object from the flow path 106 into a desired microfluidic sequestration pen. In some embodiments, DEP forces are used to prevent a micro-object within a sequestration pen (e.g., sequestration pen 124, 126, 128, or 130) from being displaced therefrom. Further, in some embodiments, DEP forces are used to selectively remove a micro-object from a sequestration pen that was previously collected in accordance with the teachings of the instant invention. In some embodiments, the DEP forces comprise optoelectronic tweezer (OET) forces.

In other embodiments, optoelectrowetting (OEW) forces are applied to one or more positions in the support structure 104 (and/or the cover 110) of the microfluidic device 100 (e.g., positions helping to define the flow path and/or the sequestration pens) via one or more electrodes (not shown) to manipulate, transport, separate and sort droplets located in the microfluidic circuit 120. For example, in some embodiments, OEW forces are applied to one or more positions in the support structure 104 (and/or the cover 110) in order to transfer a single droplet from the flow path 106 into a desired microfluidic sequestration pen. In some embodiments, OEW forces are used to prevent a droplet within a sequestration pen (e.g., sequestration pen 124, 126, 128, or 130) from being displaced therefrom. Further, in some embodiments, OEW forces are used to selectively remove a droplet from a sequestration pen that was previously collected in accordance with the teachings of the instant invention.

In some embodiments, DEP and/or OEW forces are combined with other forces, such as flow and/or gravitational force, so as to manipulate, transport, separate and sort micro-objects and/or droplets within the microfluidic circuit 120. For example, the enclosure 102 can be tilted (e.g., by tilting device 190) to position the flow path 106 and micro-objects located therein above the microfluidic sequestration pens, and the force of gravity can transport the micro-objects and/or droplets into the pens. In some embodiments, the DEP and/or OEW forces can be applied prior to the other forces. In other embodiments, the DEP and/or OEW forces can be applied after the other forces. In still other instances, the DEP and/or OEW forces can be applied at the same time as the other forces or in an alternating manner with the other forces.

Figure 2A:
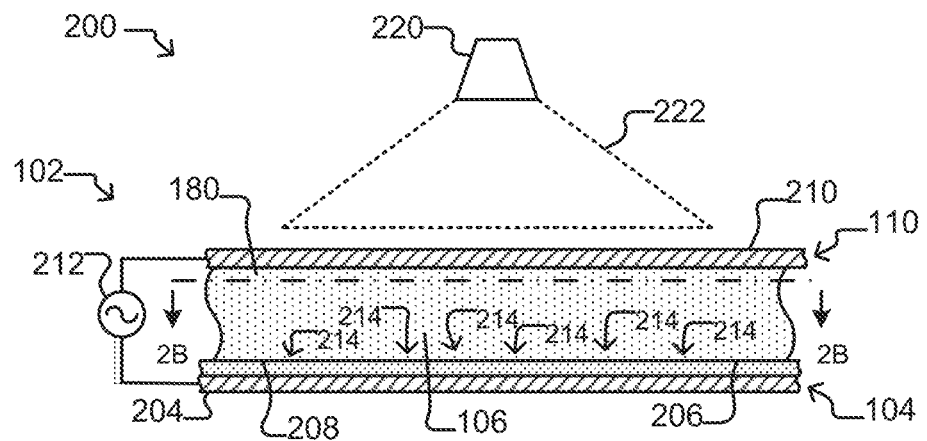
FIGS. 2A and 2B illustrate a microfluidic device according to some embodiments of the invention.

FIGS. 2A-2F illustrates various embodiments of microfluidic devices that can be used in the practice of the present invention. FIG. 2A depicts an embodiment in which the microfluidic device 200 is configured as an optically-actuated electrokinetic device. A variety of optically-actuated electrokinetic devices are known in the art, including devices having an optoelectronic tweezer (OET) configuration and devices having an opto-electrowetting (OEW) configuration. Examples of suitable OET configurations are illustrated in the following U.S. patent documents, each of which is incorporated herein by reference in its entirety: U.S. Pat. No. RE 44,711 (Wu et al.) (originally issued as U.S. Pat. No. 7,612,355); and U.S. Pat. No. 7,956,339 (Ohta et al.). Examples of OEW configurations are illustrated in U.S. Pat. No. 6,958,132 (Chiou et al.) and U.S. Patent Application Publication No. 2012/0024708 (Chiou et al.), both of which are incorporated by reference herein in their entirety. Yet another example of an optically-actuated electrokinetic device includes a combined OET/OEW configuration, examples of which are shown in U.S. Patent Publication Nos. 20150306598 (Khandros et al.) and 20150306599 (Khandros et al.) and their corresponding PCT Publications WO2015/164846 and WO2015/164847, all of which are incorporated herein by reference in their entirety.

Motive Microfluidic Device Configurations.

As described above, the control and monitoring equipment of the system can comprise a motive module 162 for selecting and moving objects, such as micro-objects or droplets, in the microfluidic circuit of a microfluidic device. The microfluidic device can have a variety of motive configurations, depending upon the type of object being moved and other considerations. For example, a dielectrophoresis (DEP) configuration can be utilized to select and move micro-objects in the microfluidic circuit. Thus, the support structure 104 and/or cover 110 of the microfluidic device 100 can comprise a DEP configuration for selectively inducing DEP forces on micro-objects in a fluidic medium 180 in the microfluidic circuit 120 and thereby select, capture, and/or move individual micro-objects or groups of micro-objects. Alternatively, the support structure 104 and/or cover 110 of the microfluidic device 100 can comprise an electrowetting (EW) configuration for selectively inducing EW forces on droplets in a fluidic medium 180 in the microfluidic circuit 120 and thereby select, capture, and/or move individual droplets or groups of droplets.

Figure 2B:
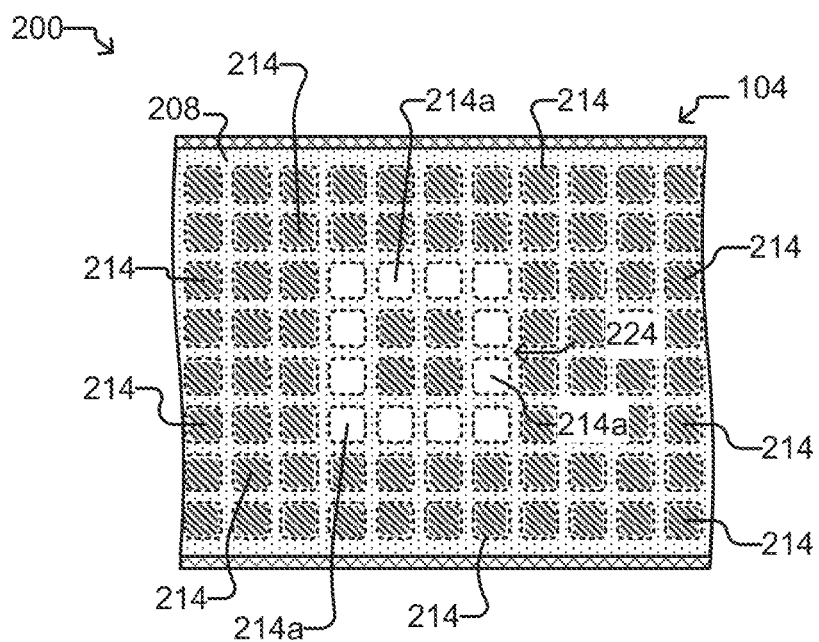

One example of a microfluidic device 200 comprising a DEP configuration is illustrated in FIGS. 2A and 2B. While for purposes of simplicity FIGS. 2A and 2B show a side cross-sectional view and a top cross-sectional view, respectively, of a portion of an enclosure 102 of the microfluidic device 200 having an open region/chamber 202, it should be understood that the region/chamber 202 may be part of a fluidic circuit element having a more detailed structure, such as a growth chamber, a sequestration pen, a flow region, or a flow channel. Furthermore, the microfluidic device 200 may include other fluidic circuit elements. For example, the microfluidic device 200 can include a plurality of growth chambers or sequestration pens and/or one or more flow regions or flow channels, such as those described herein with respect to microfluidic device 100. A DEP configuration may be incorporated into any such fluidic circuit elements of the microfluidic device 200, or select portions thereof. It should be further appreciated that any of the above or below described microfluidic device components and system components may be incorporated in and/or used in combination with the microfluidic device 200. For example, system 150 including control and monitoring equipment 152, described above, may be used with microfluidic device 200, including one or more of the media module 160, motive module 162, imaging module 164, tilting module 166, and other modules 168.

As seen in FIG. 2A, the microfluidic device 200 includes a support structure 104 having a bottom electrode 204 and an electrode activation substrate 206 overlying the bottom electrode 204, and a cover 110 having a top electrode 210, with the top electrode 210 spaced apart from the bottom electrode 204. The top electrode 210 and the electrode activation substrate 206 define opposing surfaces of the region/chamber 202. A medium 180 contained in the region/chamber 202 thus provides a resistive connection between the top electrode 210 and the electrode activation substrate 206. A power source 212 configured to be connected to the bottom electrode 204 and the top electrode 210 and create a biasing voltage between the electrodes, as required for the generation of DEP forces in the region/chamber 202, is also shown. The power source 212 can be, for example, an alternating current (AC) power source.

In certain embodiments, the microfluidic device 200 illustrated in FIGS. 2A and 2B can have an optically-actuated DEP configuration. Accordingly, changing patterns of light 222 from the light source 220, which may be controlled by the motive module 162, can selectively activate and deactivate changing patterns of DEP electrodes at regions 214 of the inner surface 208 of the electrode activation substrate 206. (Hereinafter the regions 214 of a microfluidic device having a DEP configuration are referred to as "DEP electrode regions.") As illustrated in FIG. 2B, a light pattern 222 directed onto the inner surface 208 of the electrode activation substrate 206 can illuminate select DEP electrode regions 214a (shown in white) in a pattern, such as a square. The non-illuminated DEP electrode regions 214 (cross-hatched) are hereinafter referred to as "dark" DEP electrode regions 214. The relative electrical impedance through the DEP electrode activation substrate 206 (i.e., from the bottom electrode 204 up to the inner surface 208 of the electrode activation substrate 206 which interfaces with the medium 180 in the flow region 106) is greater than the relative electrical impedance through the medium 180 in the region/chamber 202 (i.e., from the inner surface 208 of the electrode activation substrate 206 to the top electrode 210 of the cover 110) at each dark DEP electrode region 214. An illuminated DEP electrode region 214a, however, exhibits a reduced relative impedance through the electrode activation substrate 206 that is less than the relative impedance through the medium 180 in the region/chamber 202 at each illuminated DEP electrode region 214a.

With the power source 212 activated, the foregoing DEP configuration creates an electric field gradient in the fluidic medium 180 between illuminated DEP electrode regions

214a and adjacent dark DEP electrode regions 214, which in turn creates local DEP forces that attract or repel nearby micro-objects (not shown) in the fluidic medium 180. DEP electrodes that attract or repel micro-objects in the fluidic medium 180 can thus be selectively activated and deactivated at many different such DEP electrode regions 214 at the inner surface 208 of the region/chamber 202 by changing light patterns 222 projected from a light source 220 into the microfluidic device 200. Whether the DEP forces attract or repel nearby micro-objects can depend on such parameters as the frequency of the power source 212 and the dielectric properties of the medium 180 and/or micro-objects (not shown).

The square pattern 224 of illuminated DEP electrode regions 214a illustrated in FIG. 2B is an example only. Any pattern of the DEP electrode regions 214 can be illuminated (and thereby activated) by the pattern of light 222 projected into the device 200, and the pattern of illuminated/activated DEP electrode regions 214 can be repeatedly changed by changing or moving the light pattern 222.

In some embodiments, the electrode activation substrate 206 can comprise or consist of a photoconductive material. In such embodiments, the inner surface 208 of the electrode activation substrate 206 can be featureless. For example, the electrode activation substrate 206 can comprise or consist of a layer of hydrogenated amorphous silicon (a-Si:H). The a-Si:H can comprise, for example, about 8% to 40% hydrogen (calculated as 100*(the number of hydrogen atoms)/(the total number of hydrogen and silicon atoms)). The layer of a-Si:H can have a thickness of about 500 nm to about 2.0 In such embodiments, the DEP electrode regions 214 can be created anywhere and in any pattern on the inner surface 208 of the electrode activation substrate 208, in accordance with the light pattern 222. The number and pattern of the DEP electrode regions 214 thus need not be fixed, but can correspond to the light pattern 222. Examples of microfluidic devices having a DEP configuration comprising a photoconductive layer such as discussed above have been described, for example, in U.S. Pat. No. RE 44,711 (Wu et al.) (originally issued as U.S. Pat. No. 7,612,355), the entire contents of which are incorporated herein by reference.

In other embodiments, the electrode activation substrate 206 can comprise a substrate comprising a plurality of doped layers, electrically insulating layers (or regions), and electrically conductive layers that form semiconductor integrated circuits, such as is known in semiconductor fields. For example, the electrode activation substrate 206 can comprise a plurality of phototransistors, including, for example, lateral bipolar phototransistors, each phototransistor corresponding to a DEP electrode region 214. Alternatively, the electrode activation substrate 206 can comprise electrodes (e.g., conductive metal electrodes) controlled by phototransistor switches, with each such electrode corresponding to a DEP electrode region 214. The electrode activation substrate 206 can include a pattern of such phototransistors or phototransistor-controlled electrodes. The pattern, for example, can be an array of substantially square phototransistors or phototransistor-controlled electrodes arranged in rows and columns, such as shown in FIG. 2B. Alternatively, the pattern can be an array of substantially hexagonal phototransistors or phototransistor-controlled electrodes that form a hexagonal lattice. Regardless of the pattern, electric circuit elements can form electrical connections between the DEP electrode regions 214 at the inner surface 208 of the electrode activation substrate 206 and the bottom electrode 210, and those electrical connections (i.e., phototransistors or electrodes) can be selectively activated and deactivated by the light pattern 222. When not activated, each electrical connection can have high impedance such that the relative impedance through the electrode activation substrate 206 (i.e., from the bottom electrode 204 to the inner surface 208 of the electrode activation substrate 206 which interfaces with the medium 180 in the region/chamber 202) is greater than the relative impedance through the medium 180 (i.e., from the inner surface 208 of the electrode activation substrate 206 to the top electrode 210 of the cover 110) at the corresponding DEP electrode region 214. When activated by light in the light pattern 222, however, the relative impedance through the electrode activation substrate 206 is less than the relative impedance through the medium 180 at each illuminated DEP electrode region 214, thereby activating the DEP electrode at the corresponding DEP electrode region 214 as discussed above. DEP electrodes that attract or repel micro-objects (not shown) in the medium 180 can thus be selectively activated and deactivated at many different DEP electrode regions 214 at the inner surface 208 of the electrode activation substrate 206 in the region/chamber 202 in a manner determined by the light pattern 222.

Examples of microfluidic devices having electrode activation substrates that comprise phototransistors have been described, for example, in U.S. Pat. No. 7,956,339 (Ohta et al.) (see, e.g., device 300 illustrated in FIGS. 21 and 22, and descriptions thereof), the entire contents of which are incorporated herein by reference. Examples of microfluidic devices having electrode activation substrates that comprise electrodes controlled by phototransistor switches have been described, for example, in U.S. Patent Publication No. 2014/0124370 (Short et al.) (see, e.g., devices 200, 400, 500, 600, and 900 illustrated throughout the drawings, and descriptions thereof), the entire contents of which are incorporated herein by reference.

In some embodiments of a DEP configured microfluidic device, the top electrode 210 is part of a first wall (or cover 110) of the enclosure 102, and the electrode activation substrate 206 and bottom electrode 204 are part of a second wall (or support structure 104) of the enclosure 102. The region/chamber 202 can be between the first wall and the second wall. In other embodiments, the electrode 210 is part of the second wall (or support structure 104) and one or both of the electrode activation substrate 206 and/or the electrode 210 are part of the first wall (or cover 110). Moreover, the light source 220 can alternatively be used to illuminate the enclosure 102 from below.

With the microfluidic device 200 of FIGS. 2A-2B having a DEP configuration, the motive module 162 can select a micro-object (not shown) in the medium 180 in the region/chamber 202 by projecting a light pattern 222 into the device 200 to activate a first set of one or more DEP electrodes at DEP electrode regions 214a of the inner surface 208 of the electrode activation substrate 206 in a pattern (e.g., square pattern 224) that surrounds and captures the micro-object. The motive module 162 can then move the captured micro-object by moving the light pattern 222 relative to the device 200 to activate a second set of one or more DEP electrodes at DEP electrode regions 214. Alternatively, the device 200 can be moved relative to the light pattern 222.

In other embodiments, the microfluidic device 200 can have a DEP configuration that does not rely upon light activation of DEP electrodes at the inner surface 208 of the electrode activation substrate 206. For example, the electrode activation substrate 206 can comprise selectively addressable and energizable electrodes positioned opposite to a surface including at least one electrode (e.g., cover 110).

Switches (e.g., transistor switches in a semiconductor substrate) may be selectively opened and closed to activate or inactivate DEP electrodes at DEP electrode regions 214, thereby creating a net DEP force on a micro-object (not shown) in region/chamber 202 in the vicinity of the activated DEP electrodes. Depending on such characteristics as the frequency of the power source 212 and the dielectric properties of the medium (not shown) and/or micro-objects in the region/chamber 202, the DEP force can attract or repel a nearby micro-object. By selectively activating and deactivating a set of DEP electrodes (e.g., at a set of DEP electrodes regions 214 that forms a square pattern 224), one or more micro-objects in region/chamber 202 can be trapped and moved within the region/chamber 202. The motive module 162 in FIG. 1 can control such switches and thus activate and deactivate individual ones of the DEP electrodes to select, trap, and move particular micro-objects (not shown) around the region/chamber 202. Microfluidic devices having a DEP configuration that includes selectively addressable and energizable electrodes are known in the art and have been described, for example, in U.S. Pat. No. 6,294,063 (Becker et al.) and U.S. Pat. No. 6,942,776 (Medoro), the entire contents of which are incorporated herein by reference.

As yet another example, the microfluidic device 200 can have an electrowetting (EW) configuration, which can be in place of the DEP configuration or can be located in a portion of the microfluidic device 200 that is separate from the portion which has the DEP configuration. The EW configuration can be an opto-electrowetting configuration or an electrowetting on dielectric (EWOD) configuration, both of which are known in the art. In some EW configurations, the support structure 104 has an electrode activation substrate 206 sandwiched between a dielectric layer (not shown) and the bottom electrode 204. The dielectric layer can comprise a hydrophobic material and/or can be coated with a hydrophobic material. For microfluidic devices 200 that have an EW configuration, the inner surface 208 of the support structure 104 is the inner surface of the dielectric layer or its hydrophobic coating.

The dielectric layer (not shown) can comprise one or more oxide layers, and can have a thickness of about 50 nm to about 250 nm (e.g., about 125 nm to about 175 nm). In certain embodiments, the dielectric layer may comprise a layer of oxide, such as a metal oxide (e.g., aluminum oxide or hafnium oxide). In certain embodiments, the dielectric layer can comprise a dielectric material other than a metal oxide, such as silicon oxide or a nitride. Regardless of the exact composition and thickness, the dielectric layer can have an impedance of about 10 kOhms to about 50 kOhms.

In some embodiments, the surface of the dielectric layer that faces inward toward region/chamber 202 is coated with a hydrophobic material. The hydrophobic material can comprise, for example, fluorinated carbon molecules. Examples of fluorinated carbon molecules include perfluoro-polymers such as polytetrafluoroethylene (e.g., TEFLON®) or poly (2,3-difluoromethylenyl-perfluorotetrahydrofuran) (e.g., CYTOP™). Molecules that make up the hydrophobic material can be covalently bonded to the surface of the dielectric layer. For example, molecules of the hydrophobic material can be covalently bound to the surface of the dielectric layer by means of a linker, such as a siloxane group, a phosphonic acid group, or a thiol group. Thus, in some embodiments, the hydrophobic material can comprise alkyl-terminated siloxane, alkyl-termination phosphonic acid, or alkyl-terminated thiol. The alkyl group can be long-chain hydrocarbons (e.g., having a chain of at least 10 carbons, or at least 16, 18, 20, 22, or more carbons). Alternatively, fluorinated (or perfluorinated) carbon chains can be used in place of the alkyl groups. Thus, for example, the hydrophobic material can comprise fluoroalkyl-terminated siloxane, fluoroalkyl-terminated phosphonic acid, or fluoroalkyl-terminated thiol. In some embodiments, the hydrophobic coating has a thickness of about 10 nm to about 50 nm. In other embodiments, the hydrophobic coating has a thickness of less than 10 nm (e.g., less than 5 nm, or about 1.5 to 3.0 nm).

In some embodiments, the cover 110 of a microfluidic device 200 having an electrowetting configuration is coated with a hydrophobic material (not shown) as well. The hydrophobic material can be the same hydrophobic material used to coat the dielectric layer of the support structure 104, and the hydrophobic coating can have a thickness that is substantially the same as the thickness of the hydrophobic coating on the dielectric layer of the support structure 104. Moreover, the cover 110 can comprise an electrode activation substrate 206 sandwiched between a dielectric layer and the top electrode 210, in the manner of the support structure 104. The electrode activation substrate 206 and the dielectric layer of the cover 110 can have the same composition and/or dimensions as the electrode activation substrate 206 and the dielectric layer of the support structure 104. Thus, the microfluidic device 200 can have two eletrowetting surfaces.

In some embodiments, the electrode activation substrate 206 can comprise a photoconductive material, such as described above. Accordingly, in certain embodiments, the electrode activation substrate 206 can comprise or consist of a layer of hydrogenated amorphous silicon (a-Si:H). The a-Si:H can comprise, for example, about 8% to 40% hydrogen (calculated as 100*(the number of hydrogen atoms)/(the total number of hydrogen and silicon atoms)). The layer of a-Si:H can have a thickness of about 500 nm to about 2.0 μm. Alternatively, the electrode activation substrate 206 can comprise electrodes (e.g., conductive metal electrodes) controlled by phototransistor switches, as described above. Microfluidic devices having an opto-electrowetting configuration are known in the art and/or can be constructed with electrode activation substrates known in the art. For example, U.S. Pat. No. 6,958,132 (Chiou et al.), the entire contents of which are incorporated herein by reference, discloses opto-electrowetting configurations having a photoconductive material such as a-Si:H, while U.S. Patent Publication No. 2014/0124370 (Short et al.), referenced above, discloses electrode activation substrates having electrodes controlled by phototransistor switches.

The microfluidic device 200 thus can have an opto-electrowetting configuration, and light patterns 222 can be used to activate photoconductive EW regions or photoresponsive EW electrodes in the electrode activation substrate 206. Such activated EW regions or EW electrodes of the electrode activation substrate 206 can generate an electrowetting force at the inner surface 208 of the support structure 104 (i.e., the inner surface of the overlaying dielectric layer or its hydrophobic coating). By changing the light patterns 222 (or moving microfluidic device 200 relative to the light source 220) incident on the electrode activation substrate 206, droplets (e.g., containing an aqueous medium, solution, or solvent) contacting the inner surface 208 of the support structure 104 can be moved through an immiscible fluid (e.g., an oil medium) present in the region/chamber 202.

In other embodiments, microfluidic devices 200 can have an EWOD configuration, and the electrode activation substrate 206 can comprise selectively addressable and energizable electrodes that do not rely upon light for activation.

The electrode activation substrate 206 thus can include a pattern of such electrowetting (EW) electrodes. The pattern, for example, can be an array of substantially square EW electrodes arranged in rows and columns, such as shown in FIG. 2B. Alternatively, the pattern can be an array of substantially hexagonal EW electrodes that form a hexagonal lattice. Regardless of the pattern, the EW electrodes can be selectively activated (or deactivated) by electrical switches (e.g., transistor switches in a semiconductor substrate). By selectively activating and deactivating EW electrodes in the electrode activation substrate 206, droplets (not shown) contacting the inner surface 208 of the overlaying dielectric layer or its hydrophobic coating can be moved within the region/chamber 202. The motive module 162 in FIG. 1 can control such switches and thus activate and deactivate individual EW electrodes to select and move particular droplets around region/chamber 202. Microfluidic devices having a EWOD configuration with selectively addressable and energizable electrodes are known in the art and have been described, for example, in U.S. Pat. No. 8,685,344 (Sundarsan et al.), the entire contents of which are incorporated herein by reference.

Regardless of the configuration of the microfluidic device 200, a power source 212 can be used to provide a potential (e.g., an AC voltage potential) that powers the electrical circuits of the microfluidic device 200. The power source 212 can be the same as, or a component of, the power source 192 referenced in FIG. 1. Power source 212 can be configured to provide an AC voltage and/or current to the top electrode 210 and the bottom electrode 204. For an AC voltage, the power source 212 can provide a frequency range and an average or peak power (e.g., voltage or current) range sufficient to generate net DEP forces (or electrowetting forces) strong enough to trap and move individual micro-objects (not shown) in the region/chamber 202, as discussed above, and/or to change the wetting properties of the inner surface 208 of the support structure 104 (i.e., the dielectric layer and/or the hydrophobic coating on the dielectric layer) in the region/chamber 202, as also discussed above. Such frequency ranges and average or peak power ranges are known in the art. See, e.g., U.S. Pat. No. 6,958,132 (Chiou et al.), U.S. Pat. No. RE44,711 (Wu et al.) (originally issued as U.S. Pat. No. 7,612,355), and US Patent Application Publication Nos. US2014/0124370 (Short et al.), US2015/0306598 (Khandros et al.), and US2015/0306599 (Khandros et al.).

Sequestration Pens.

Figure 2C:
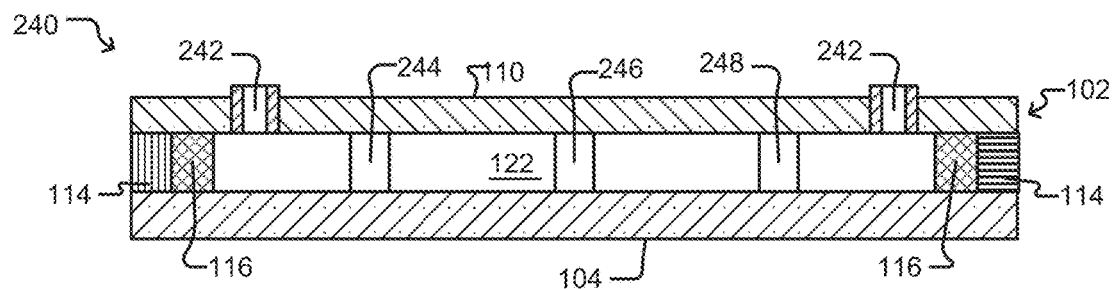
FIGS. 2C and 2D illustrate sequestration pens according to some embodiments of the invention.
Figure 2D:
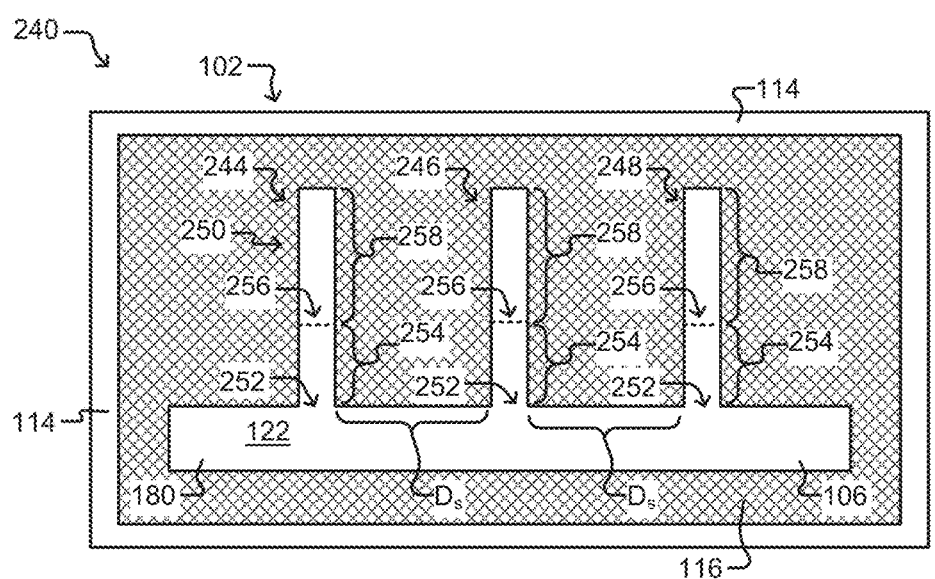

Non-limiting examples of generic sequestration pens 244, 246, and 248 are shown within the microfluidic device 240 depicted in FIGS. 2C and 2D. Each sequestration pen 244, 246, and 248 can comprise an isolation structure 250 defining an isolation region 258 and a connection region 254 fluidically connecting the isolation region 258 to a channel 122. The connection region 254 can comprise a proximal opening 252 to the channel 122 and a distal opening 256 to the isolation region 258. The connection region 254 can be configured so that the maximum penetration depth of a flow of a fluidic medium (not shown) flowing from the channel 122 into the sequestration pen 244, 246, 248 does not extend into the isolation region 258. Thus, due to the connection region 254, a micro-object (not shown) or other material (not shown) disposed in an isolation region 258 of a sequestration pen 244, 246, 248 can thus be isolated from, and not substantially affected by, a flow of medium 180 in the channel 122.

The channel 122 can thus be an example of a swept region, and the isolation regions 258 of the sequestration pens 244, 246, 248 can be examples of unswept regions. As noted, the channel 122 and sequestration pens 244, 246, 248 can be configured to contain one or more fluidic media 180. In the example shown in FIGS. 2C-2D, the ports 242 are connected to the channel 122 and allow a fluidic medium 180 to be introduced into or removed from the microfluidic device 240. Once the microfluidic device 240 contains the fluidic medium 180, the flow 260 of fluidic medium 180 in the channel 122 can be selectively generated and stopped. For example, as shown, the ports 242 can be disposed at different locations (e.g., opposite ends) of the channel 122, and a flow 260 of medium can be created from one port 242 functioning as an inlet to another port 242 functioning as an outlet.

Figure 2E:
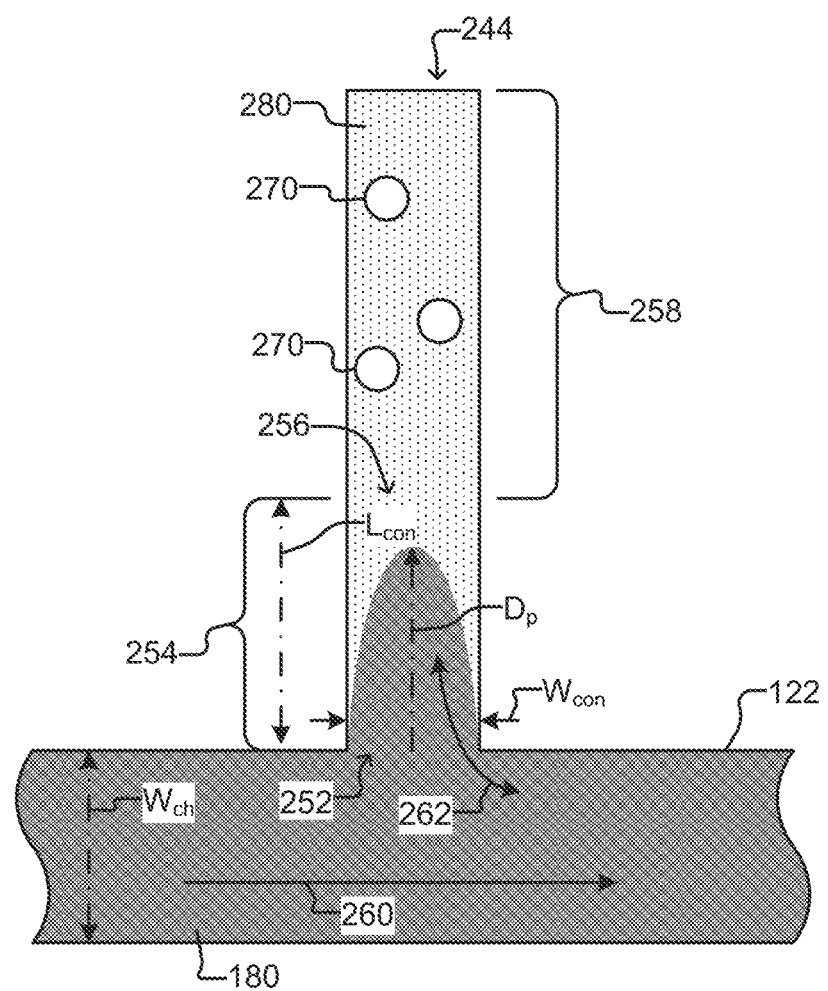
FIG. 2E illustrates a detailed sequestration pen according to some embodiments of the invention.

FIG. 2E illustrates a detailed view of an example of a sequestration pen 244 according to the present invention. Examples of micro-objects 270 are also shown.

As is known, a flow 260 of fluidic medium 180 in a microfluidic channel 122 past a proximal opening 252 of sequestration pen 244 can cause a secondary flow 262 of the medium 180 into and/or out of the sequestration pen 244. To isolate micro-objects 270 in the isolation region 258 of a sequestration pen 244 from the secondary flow 262, the length $L_{con}$ of the connection region 254 of the sequestration pen 244 (i.e., from the proximal opening 252 to the distal opening 256) should be greater than the penetration depth $D_p$ of the secondary flow 262 into the connection region 254. The penetration depth $D_p$ of the secondary flow 262 depends upon the velocity of the fluidic medium 180 flowing in the channel 122 and various parameters relating to the configuration of the channel 122 and the proximal opening 252 of the connection region 254 to the channel 122. For a given microfluidic device, the configurations of the channel 122 and the opening 252 will be fixed, whereas the rate of flow 260 of fluidic medium 180 in the channel 122 will be variable. Accordingly, for each sequestration pen 244, a maximal velocity $V_{max}$ for the flow 260 of fluidic medium 180 in channel 122 can be identified that ensures that the penetration depth $D_p$ of the secondary flow 262 does not exceed the length $L_{con}$ of the connection region 254. As long as the rate of the flow 260 of fluidic medium 180 in the channel 122 does not exceed the maximum velocity $V_{max}$, the resulting secondary flow 262 can be limited to the channel 122 and the connection region 254 and kept out of the isolation region 258. The flow 260 of medium 180 in the channel 122 will thus not draw micro-objects 270 out of the isolation region 258. Rather, micro-objects 270 located in the isolation region 258 will stay in the isolation region 258 regardless of the flow 260 of fluidic medium 180 in the channel 122.

Moreover, as long as the rate of flow 260 of medium 180 in the channel 122 does not exceed $V_{max}$, the flow 260 of fluidic medium 180 in the channel 122 will not move miscellaneous particles (e.g., microparticles and/or nanoparticles) from the channel 122 into the isolation region 258 of a sequestration pen 244. Having the length $L_{con}$ of the connection region 254 be greater than the maximum penetration depth $D_p$ of the secondary flow 262 can thus prevent contamination of one sequestration pen 244 with miscellaneous particles from the channel 122 or another sequestration pen (e.g., sequestration pens 246, 248 in FIG. 2D).

Because the channel 122 and the connection regions 254 of the sequestration pens 244, 246, 248 can be affected by the flow 260 of medium 180 in the channel 122, the channel 122 and connection regions 254 can be deemed swept (or flow) regions of the microfluidic device 240. The isolation regions 258 of the sequestration pens 244, 246, 248, on the other hand, can be deemed unswept (or non-flow) regions. For example, components (not shown) in a first fluidic medium 180 in the channel 122 can mix with a second fluidic medium 280 in the isolation region 258 substantially only by diffusion of components of the first medium 180 from the channel 122 through the connection region 254 and into the second fluidic medium 280 in the isolation region 258. Similarly, components (not shown) of the second medium 280 in the isolation region 258 can mix with the first medium 180 in the channel 122 substantially only by diffusion of components of the second medium 280 from the isolation region 258 through the connection region 254 and into the first medium 180 in the channel 122. The first medium 180 can be the same medium or a different medium than the second medium 280. Moreover, the first medium 180 and the second medium 280 can start out being the same, then become different (e.g., through conditioning of the second medium 280 by one or more cells in the isolation region 258, or by changing the medium 180 flowing through the channel 122).

The maximum penetration depth $D_p$ of the secondary flow 262 caused by the flow 260 of fluidic medium 180 in the channel 122 can depend on a number of parameters, as mentioned above. Examples of such parameters include: the shape of the channel 122 (e.g., the channel can direct medium into the connection region 254, divert medium away from the connection region 254, or direct medium in a direction substantially perpendicular to the proximal opening 252 of the connection region 254 to the channel 122); a width $W_{ch}$ (or cross-sectional area) of the channel 122 at the proximal opening 252; and a width $W_{con}$ (or cross-sectional area) of the connection region 254 at the proximal opening 252; the velocity V of the flow 260 of fluidic medium 180 in the channel 122; the viscosity of the first medium 180 and/or the second medium 280, or the like.

In some embodiments, the dimensions of the channel 122 and sequestration pens 244, 246, 248 can be oriented as follows with respect to the vector of the flow 260 of fluidic medium 180 in the channel 122: the channel width $W_{ch}$ (or cross-sectional area of the channel 122) can be substantially perpendicular to the flow 260 of medium 180; the width $W_{con}$ (or cross-sectional area) of the connection region 254 at opening 252 can be substantially parallel to the flow 260 of medium 180 in the channel 122; and/or the length $L_{con}$ of the connection region can be substantially perpendicular to the flow 260 of medium 180 in the channel 122. The foregoing are examples only, and the relative position of the channel 122 and sequestration pens 244, 246, 248 can be in other orientations with respect to each other.

As illustrated in FIG. 2E, the width $W_{con}$ of the connection region 254 can be uniform from the proximal opening 252 to the distal opening 256. The width $W_{con}$ of the connection region 254 at the distal opening 256 can thus be in any of the ranges identified herein for the width $W_{con}$ of the connection region 254 at the proximal opening 252. Alternatively, the width $W_{con}$ of the connection region 254 at the distal opening 256 can be larger than the width $W_{con}$ of the connection region 254 at the proximal opening 252.

As illustrated in FIG. 2E, the width of the isolation region 258 at the distal opening 256 can be substantially the same as the width $W_{con}$ of the connection region 254 at the proximal opening 252. The width of the isolation region 258 at the distal opening 256 can thus be in any of the ranges identified herein for the width $W_{con}$ of the connection region 254 at the proximal opening 252. Alternatively, the width of the isolation region 258 at the distal opening 256 can be larger or smaller than the width $W_{con}$ of the connection region 254 at the proximal opening 252. Moreover, the distal opening 256 may be smaller than the proximal opening 252 and the width $W_{con}$ of the connection region 254 may be narrowed between the proximal opening 252 and distal opening 256. For example, the connection region 254 may be narrowed between the proximal opening and the distal opening, using a variety of different geometries (e.g. chamfering the connection region, beveling the connection region). Further, any part or subpart of the connection region 254 may be narrowed (e.g. a portion of the connection region adjacent to the proximal opening 252).

In various embodiments of sequestration pens (e.g. 124, 126, 128, 130, 244, 246 or 248), the isolation region (e.g. 258) is configured to contain a plurality of micro-objects. In other embodiments, the isolation region can be configured to contain only one, two, three, four, five, or a similar relatively small number of micro-objects. Accordingly, the volume of an isolation region can be, for example, at least $3\times10^3$, $6\times10^3$, $9\times10^3$, $1\times10^4$, $2\times10^4$, $4\times10^4$, $8\times10^4$, $1\times10^5$, $2\times10^5$, $4\times10^5$, $8\times10^5$, $1\times10^6$, $2\times10^6$, $4\times10^6$, $6\times10^6$ cubic microns, or more.

In various embodiments of sequestration pens, the width $W_{ch}$ of the channel 122 at a proximal opening (e.g. 252) can be within any of the following ranges: 50-1000 microns, 50-500 microns, 50-400 microns, 50-300 microns, 50-250 microns, 50-200 microns, 50-150 microns, 50-100 microns, 70-500 microns, 70-400 microns, 70-300 microns, 70-250 microns, 70-200 microns, 70-150 microns, 90-400 microns, 90-300 microns, 90-250 microns, 90-200 microns, 90-150 microns, 100-300 microns, 100-250 microns, 100-200 microns, 100-150 microns, and 100-120 microns. The foregoing are examples only, and the width $W_{ch}$ of the channel 122 can be in other ranges (e.g., a range defined by any of the endpoints listed above). Moreover, the $W_{ch}$ of the channel 122 can be selected to be in any of these ranges in regions of the channel other than at a proximal opening of a sequestration pen.

In some embodiments, a sequestration pen has a cross-sectional height of about 30 to about 200 microns, or about 50 to about 150 microns. In some embodiments, the sequestration pen has a cross-sectional area of about 100,000 to about 2,500,000 square microns, or about 200,000 to about 2,000,000 square microns. In some embodiments, a connection region has a cross-sectional height that matches the cross-sectional height of the corresponding sequestration pen. In some embodiments, the connection region has a cross-sectional width of about 50 to about 500 microns, or about 100 to about 300 microns.

In various embodiments of sequestration pens the height $H_{ch}$ of the channel 122 at a proximal opening 252 can be within any of the following ranges: 20-100 microns, 20-90 microns, 20-80 microns, 20-70 microns, 20-60 microns, 20-50 microns, 30-100 microns, 30-90 microns, 30-80 microns, 30-70 microns, 30-60 microns, 30-50 microns, 40-100 microns, 40-90 microns, 40-80 microns, 40-70 microns, 40-60 microns, or 40-50 microns. The foregoing are examples only, and the height $H_{ch}$ of the channel 122 can be in other ranges (e.g., a range defined by any of the endpoints listed above). The height $H_{ch}$ of the channel 122 can be selected to be in any of these ranges in regions of the channel other than at a proximal opening of a sequestration pen.

In various embodiments of sequestration pens a cross-sectional area of the channel 122 at a proximal opening 252 can be within any of the following ranges: 500-50,000 square microns, 500-40,000 square microns, 500-30,000 square microns, 500-25,000 square microns, 500-20,000 square microns, 500-15,000 square microns, 500-10,000 square microns, 500-7,500 square microns, 500-5,000 square microns, 1,000-25,000 square microns, 1,000-20,000 square microns, 1,000-15,000 square microns, 1,000-10,000 square microns, 1,000-7,500 square microns, 1,000-5,000 square microns, 2,000-20,000 square microns, 2,000-15,000 square microns, 2,000-10,000 square microns, 2,000-7,500 square microns, 2,000-6,000 square microns, 3,000-20,000 square microns, 3,000-15,000 square microns, 3,000-10,000 square microns, 3,000-7,500 square microns, or 3,000 to 6,000 square microns. The foregoing are examples only, and the cross-sectional area of the channel 122 at a proximal opening 252 can be in other ranges (e.g., a range defined by any of the endpoints listed above).

In various embodiments of sequestration pens, the length $L_{con}$ of the connection region 254 can be in any of the following ranges: 1-200 microns, 5-150 microns, 10-100 microns, 15-80 microns, 20-60 microns, 20-500 microns, 40-400 microns, 60-300 microns, 80-200 microns, and 100-150 microns. The foregoing are examples only, and length $L_{con}$ of a connection region 254 can be in a different ranges than the foregoing examples (e.g., a range defined by any of the endpoints listed above).

In various embodiments of sequestration pens the width $W_{con}$ of a connection region 254 at a proximal opening 252 can be in any of the following ranges: 20-500 microns, 20-400 microns, 20-300 microns, 20-200 microns, 20-150 microns, 20-100 microns, 20-80 microns, 20-60 microns, 30-400 microns, 30-300 microns, 30-200 microns, 30-150 microns, 30-100 microns, 30-80 microns, 30-60 microns, 40-300 microns, 40-200 microns, 40-150 microns, 40-100 microns, 40-80 microns, 40-60 microns, 50-250 microns, 50-200 microns, 50-150 microns, 50-100 microns, 50-80 microns, 60-200 microns, 60-150 microns, 60-100 microns, 60-80 microns, 70-150 microns, 70-100 microns, and 80-100 microns. The foregoing are examples only, and the width $W_{con}$ of a connection region 254 at a proximal opening 252 can be different than the foregoing examples (e.g., a range defined by any of the endpoints listed above).

In various embodiments of sequestration pens the width $W_{con}$ of a connection region 254 at a proximal opening 252 can be in any of the following ranges: 2-35 microns, 2-25 microns, 2-20 microns, 2-15 microns, 2-10 microns, 2-7 microns, 2-5 microns, 2-3 microns, 3-25 microns, 3-20 microns, 3-15 microns, 3-10 microns, 3-7 microns, 3-5 microns, 3-4 microns, 4-20 microns, 4-15 microns, 4-10 microns, 4-7 microns, 4-5 microns, 5-15 microns, 5-10 microns, 5-7 microns, 6-15 microns, 6-10 microns, 6-7 microns, 7-15 microns, 7-10 microns, 8-15 microns, and 8-10 microns. The foregoing are examples only, and the width $W_{con}$ of a connection region 254 at a proximal opening 252 can be different than the foregoing examples (e.g., a range defined by any of the endpoints listed above).

In various embodiments of sequestration pens, a ratio of the length $L_{con}$ of a connection region 254 to a width $W_{con}$ of the connection region 254 at the proximal opening 252 can be greater than or equal to any of the following ratios: 0.5, 1.0, 1.5, 2.0, 2.5, 3.0, 3.5, 4.0, 4.5, 5.0, 6.0, 7.0, 8.0, 9.0, 10.0, or more. The foregoing are examples only, and the ratio of the length $L_{con}$ of a connection region 254 to a width $W_{con}$ of the connection region 254 at the proximal opening 252 can be different than the foregoing examples.

In various embodiments of microfluidic devices 100, 200, 240, 290, $V_{max}$ can be set around 0.2, 0.3, 0.4, 0.5, 0.6, 0.7, 0.8, 0.9, 1.0, 1.1, 1.2, 1.3, 1.4, or 1.5 µL/sec.

In various embodiments of microfluidic devices having sequestration pens, the volume of an isolation region 258 of a sequestration pen can be, for example, at least $3 \times 10^3$, $6 \times 10^3$, $9 \times 10^3$, $1 \times 10^4$, $2 \times 10^4$, $4 \times 10^4$, $8 \times 10^4$, $1 \times 10^5$, $2 \times 10^5$, $4 \times 10^5$, $8 \times 10^5$, $1 \times 10^6$, $2 \times 10^6$, $4 \times 10^6$, $6 \times 10^6$ cubic microns, or more. In various embodiments of microfluidic devices having sequestration pens, the volume of a sequestration pen may be about $5 \times 10^3$, $7 \times 10^3$, $1 \times 10^4$, $3 \times 10^4$, $5 \times 10^4$, $8 \times 10^4$, $1 \times 10^5$, $2 \times 10^5$, $4 \times 10^5$, $6 \times 10^5$, $8 \times 10^5$, $1 \times 10^6$, $2 \times 10^6$, $4 \times 10^6$, $8 \times 10^6$, $1 \times 10^7$, $3 \times 10^7$, $5 \times 10^7$, or about $8 \times 10^7$ cubic microns, or more. In some embodiments, the microfluidic device has sequestration pens wherein no more than $1 \times 10^2$ biological cells may be maintained, and the volume of a sequestration pen may be no more than $2 \times 10^6$ cubic microns. In some embodiments, the microfluidic device has sequestration pens wherein no more than $1 \times 10^2$ biological cells may be maintained, and a sequestration pen may be no more than $4 \times 10^5$ cubic microns. In yet other embodiments, the microfluidic device has sequestration pens wherein no more than 50 biological cells may be maintained, a sequestration pen may be no more than $4 \times 10^5$ cubic microns.

In various embodiment, the microfluidic device has sequestration pens configured as in any of the embodiments discussed herein where the microfluidic device has about 100 to about 500 sequestration pens; about 200 to about 1000 sequestration pens, about 500 to about 1500 sequestration pens, about 1000 to about 2000 sequestration pens, or about 1000 to about 3500 sequestration pens.

In some other embodiments, the microfluidic device has sequestration pens configured as in any of the embodiments discussed herein where the microfluidic device has about 1500 to about 3000 sequestration pens, about 2000 to about 3500 sequestration pens, about 2500 to about 4000 sequestration pens, about 3000 to about 4500 sequestration pens, about 3500 to about 5000 sequestration pens, about 4000 to about 5500 sequestration pens, about 4500 to about 6000 sequestration pens, about 5000 to about 6500 sequestration pens, about 5500 to about 7000 sequestration pens, about 6000 to about 7500 sequestration pens, about 6500 to about 8000 sequestration pens, about 7000 to about 8500 sequestration pens, about 7500 to about 9000 sequestration pens, about 8000 to about 9500 sequestration pens, about 8500 to about 10,000 sequestration pens, about 9000 to about 10,500 sequestration pens, about 9500 to about 11,000 sequestration pens, about 10,000 to about 11,500 sequestration pens, about 10,500 to about 12,000 sequestration pens, about 11,000 to about 12,500 sequestration pens, about 11,500 to about 13,000 sequestration pens, about 12,000 to about 13,500 sequestration pens, about 12,500 to about 14,000 sequestration pens, about 13,000 to about 14,500 sequestration pens, about 13,500 to about 15,000 sequestration pens, about 14,000 to about 15,500 sequestration pens, about 14,500 to about 16,000 sequestration pens, about 15,000 to about 16,500 sequestration pens, about 15,500 to about 17,000 sequestration pens, about 16,000 to about 17,500 sequestration pens, about 16,500 to about 18,000 sequestration pens, about 17,000 to about 18,500 sequestration pens, about 17,500 to about 19,000 sequestration pens, about 18,000 to about 19,500 sequestration pens, about 18,500 to about 20,000 sequestration pens, about 19,000 to about 20,500 sequestration pens, about 19,500 to about 21,000 sequestration pens, or about 20,000 to about 21,500 sequestration pens.

Figure 2F:
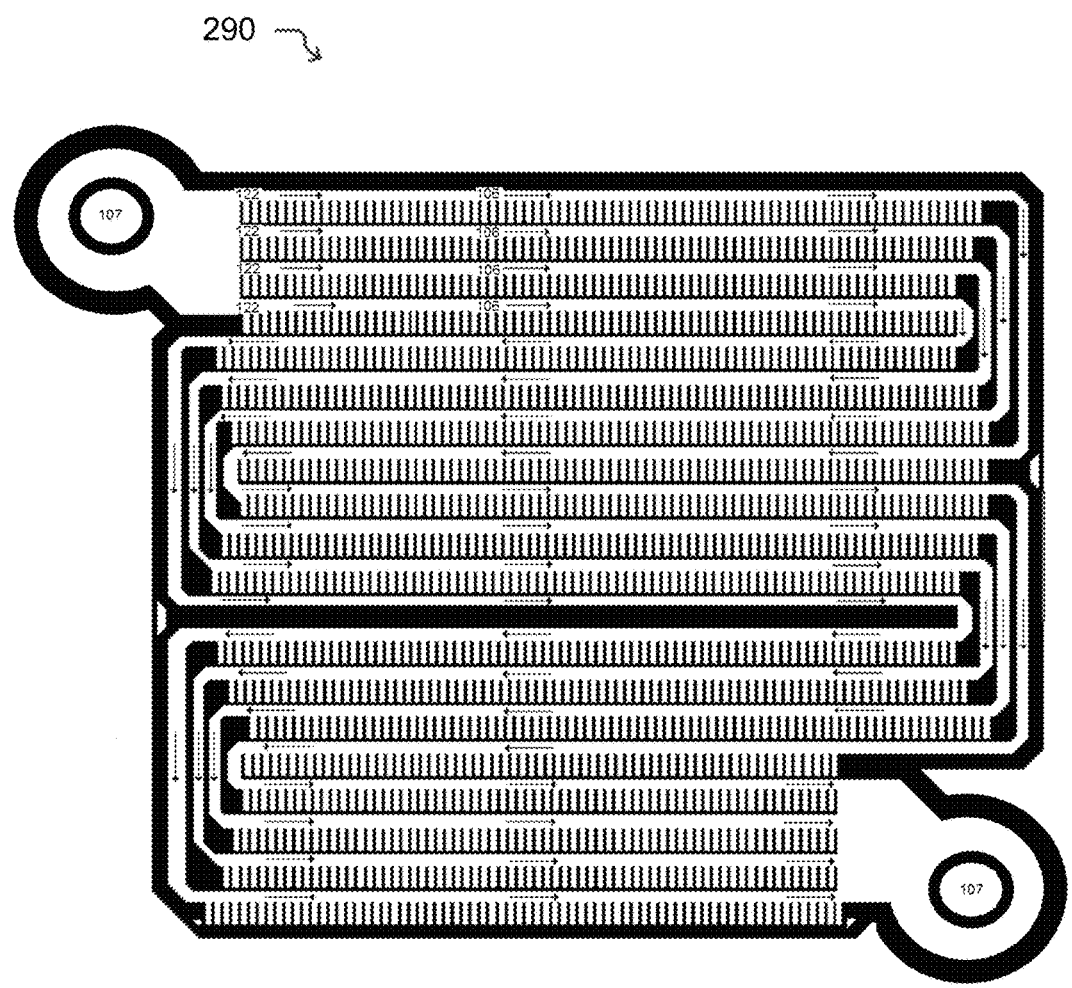
FIG. 2F illustrates a microfluidic device according to an embodiment of the invention.

FIG. 2F illustrates a microfluidic device 290 according to one embodiment. The microfluidic device 290 is illustrated in FIG. 2F is a stylized diagram of a microfluidic device 100. In practice the microfluidic device 290 and its constituent circuit elements (e.g. channels 122 and sequestration pens 128) would have the dimensions discussed herein. The microfluidic circuit 120 illustrated in FIG. 2F has two ports 107, four distinct channels 122 and four distinct flow paths 106. The microfluidic device 290 further comprises a plurality of sequestration pens opening off of each channel 122. In the microfluidic device illustrated in FIG. 2F, the sequestration pens have a geometry similar to the pens illustrated in FIG. 2E and thus, have both connection regions and isolation regions. Accordingly, the microfluidic circuit 120 includes both swept regions (e.g. channels 122 and portions of the connection regions 254 within the maximum penetration depth $D_p$ of the secondary flow 262) and non-swept regions (e.g. isolation regions 258 and portions of the connection regions 254 not within the maximum penetration depth $D_p$ of the secondary flow 262).

Figure 3A:
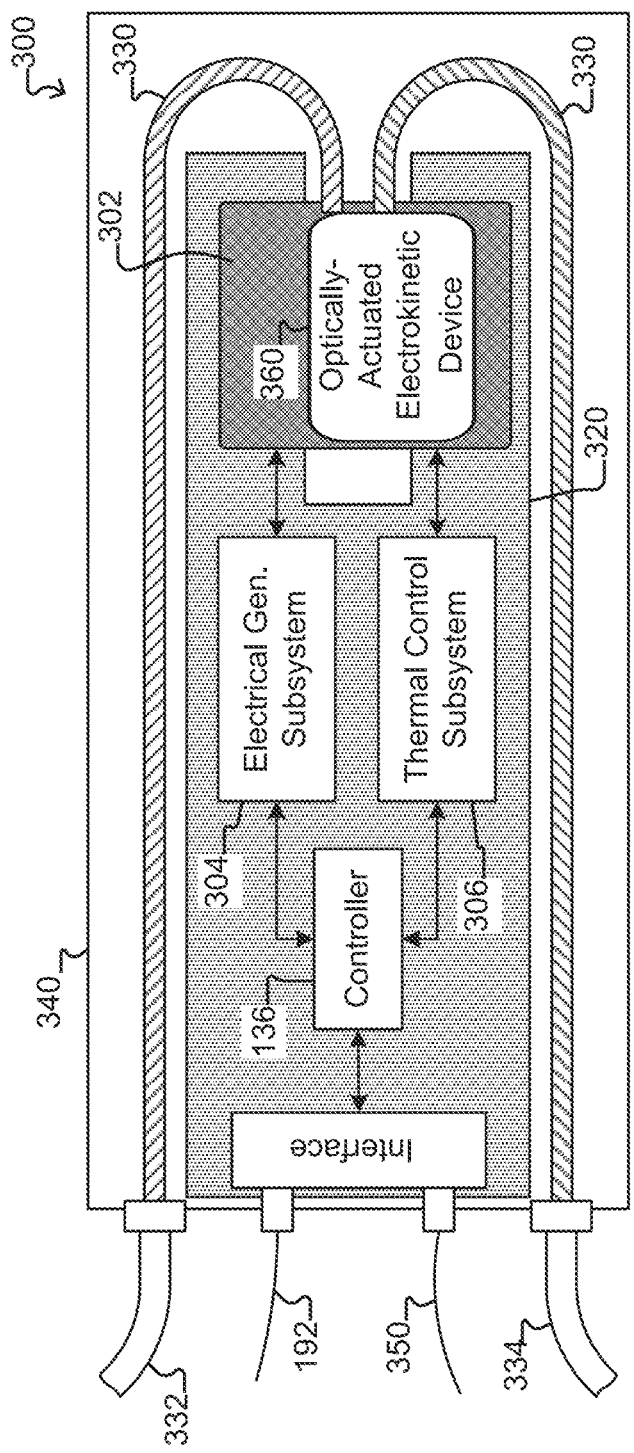
FIG. 3A illustrates a specific example of a system for use with a microfluidic device and associated control equipment according to some embodiments of the invention.
Figure 3B:
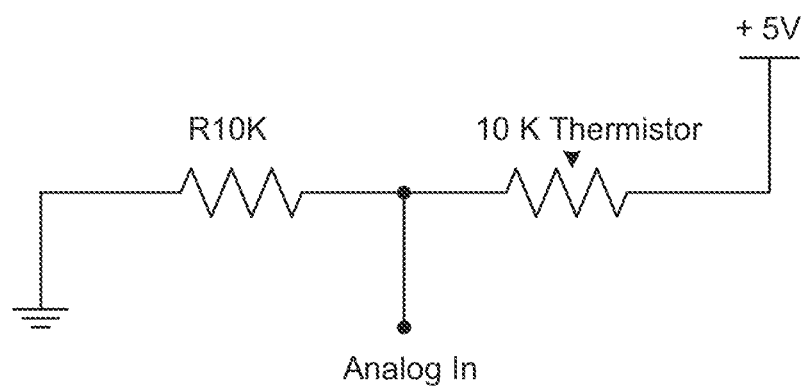
FIG. 3B illustrates an exemplary analog voltage divider circuit according to some embodiments of the invention.

FIGS. 3A through 3D shows various embodiments of system 150 which can be used to operate and observe microfluidic devices (e.g. 100, 200, 240, 290) according to the present invention. As illustrated in FIG. 3A, the system 150 can include a structure ("nest") 300 configured to hold a microfluidic device 100 (not shown), or any other microfluidic device described herein. The nest 300 can include a socket 302 capable of interfacing with the microfluidic device 360 (e.g., an optically-actuated electrokinetic device 100) and providing electrical connections from power source 192 to microfluidic device 360. The nest 300 can further include an integrated electrical signal generation subsystem 304. The electrical signal generation subsystem 304 can be configured to supply a biasing voltage to socket 302 such that the biasing voltage is applied across a pair of electrodes in the microfluidic device 360 when it is being held by socket 302. Thus, the electrical signal generation subsystem 304 can be part of power source 192. The ability to apply a biasing voltage to microfluidic device 360 does not mean that a biasing voltage will be applied at all times when the microfluidic device 360 is held by the socket 302. Rather, in most cases, the biasing voltage will be applied intermittently, e.g., only as needed to facilitate the generation of electrokinetic forces, such as dielectrophoresis or electro-wetting, in the microfluidic device 360.

As illustrated in FIG. 3A, the nest 300 can include a printed circuit board assembly (PCBA) 320. The electrical signal generation subsystem 304 can be mounted on and electrically integrated into the PCBA 320. The exemplary support includes socket 302 mounted on PCBA 320, as well.

Typically, the electrical signal generation subsystem 304 will include a waveform generator (not shown). The electrical signal generation subsystem 304 can further include an oscilloscope (not shown) and/or a waveform amplification circuit (not shown) configured to amplify a waveform received from the waveform generator. The oscilloscope, if present, can be configured to measure the waveform supplied to the microfluidic device 360 held by the socket 302. In certain embodiments, the oscilloscope measures the waveform at a location proximal to the microfluidic device 360 (and distal to the waveform generator), thus ensuring greater accuracy in measuring the waveform actually applied to the device. Data obtained from the oscilloscope measurement can be, for example, provided as feedback to the waveform generator, and the waveform generator can be configured to adjust its output based on such feedback. An example of a suitable combined waveform generator and oscilloscope is the Red Pitaya™.

In certain embodiments, the nest 300 further comprises a controller 308, such as a microprocessor used to sense and/or control the electrical signal generation subsystem 304. Examples of suitable microprocessors include the Arduino™ microprocessors, such as the Arduino Nano™.

The controller 308 may be used to perform functions and analysis or may communicate with an external master controller 154 (shown in FIG. 1) to perform functions and analysis. In the embodiment illustrated in FIG. 3A the controller 308 communicates with a master controller 154 through an interface 310 (e.g., a plug or connector).

In some embodiments, the nest 300 can comprise an electrical signal generation subsystem 304 comprising a Red Pitaya™ waveform generator/oscilloscope unit ("Red Pitaya™ unit") and a waveform amplification circuit that amplifies the waveform generated by the Red Pitaya™ unit and passes the amplified voltage to the microfluidic device 100. In some embodiments, the Red Pitaya™ unit is configured to measure the amplified voltage at the microfluidic device 360 and then adjust its own output voltage as needed such that the measured voltage at the microfluidic device 360 is the desired value. In some embodiments, the waveform amplification circuit can have a +6.5V to −6.5V power supply generated by a pair of DC-DC converters mounted on the PCBA 320, resulting in a signal of up to 13 Vpp at the microfluidic device 360.

As illustrated in FIG. 3A, the nest 300 can further include a thermal control subsystem 306. The thermal control subsystem 306 can be configured to regulate the temperature of microfluidic device 360 held by the support structure 300. For example, the thermal control subsystem 306 can include a Peltier thermoelectric device (not shown) and a cooling unit (not shown). The Peltier thermoelectric device can have a first surface configured to interface with at least one surface of the microfluidic device 360. The cooling unit can be, for example, a cooling block (not shown), such as a liquid-cooled aluminum block. A second surface of the Peltier thermoelectric device (e.g., a surface opposite the first surface) can be configured to interface with a surface of such a cooling block. The cooling block can be connected to a fluidic path 330 configured to circulate cooled fluid through the cooling block. In the embodiment illustrated in FIG. 3A, the support structure 300 comprises an inlet 332 and an outlet 334 to receive cooled fluid from an external reservoir (not shown), introduce the cooled fluid into the fluidic path 330 and through the cooling block, and then return the cooled fluid to the external reservoir. In some embodiments, the Peltier thermoelectric device, the cooling unit, and/or the fluidic path 330 can be mounted on a casing 340 of the support structure 300. In some embodiments, the thermal control subsystem 306 is configured to regulate the temperature of the Peltier thermoelectric device so as to achieve a target temperature for the microfluidic device 360. Temperature regulation of the Peltier thermoelectric device can be achieved, for example, by a thermoelectric power supply, such as a Pololu™ thermoelectric power supply (Pololu Robotics and Electronics Corp.). The thermal control subsystem 306 can include a feedback circuit, such as a temperature value provided by an analog circuit. Alternatively, the feedback circuit can be provided by a digital circuit.

In some embodiments, the nest 300 can include a thermal control subsystem 306 with a feedback circuit that is an analog voltage divider circuit (shown in FIG. 3B) which includes a resistor (e.g., with resistance 1 kOhm+/−0.1%, temperature coefficient +/−0.02 ppm/C0) and a NTC thermistor (e.g., with nominal resistance 1 kOhm+/−0.01%). In some instances, the thermal control subsystem 306 measures the voltage from the feedback circuit and then uses the calculated temperature value as input to an on-board PID control loop algorithm. Output from the PID control loop algorithm can drive, for example, both a directional and a pulse-width-modulated signal pin on a Pololu™ motor drive (not shown) to actuate the thermoelectric power supply, thereby controlling the Peltier thermoelectric device.

Figure 3C:
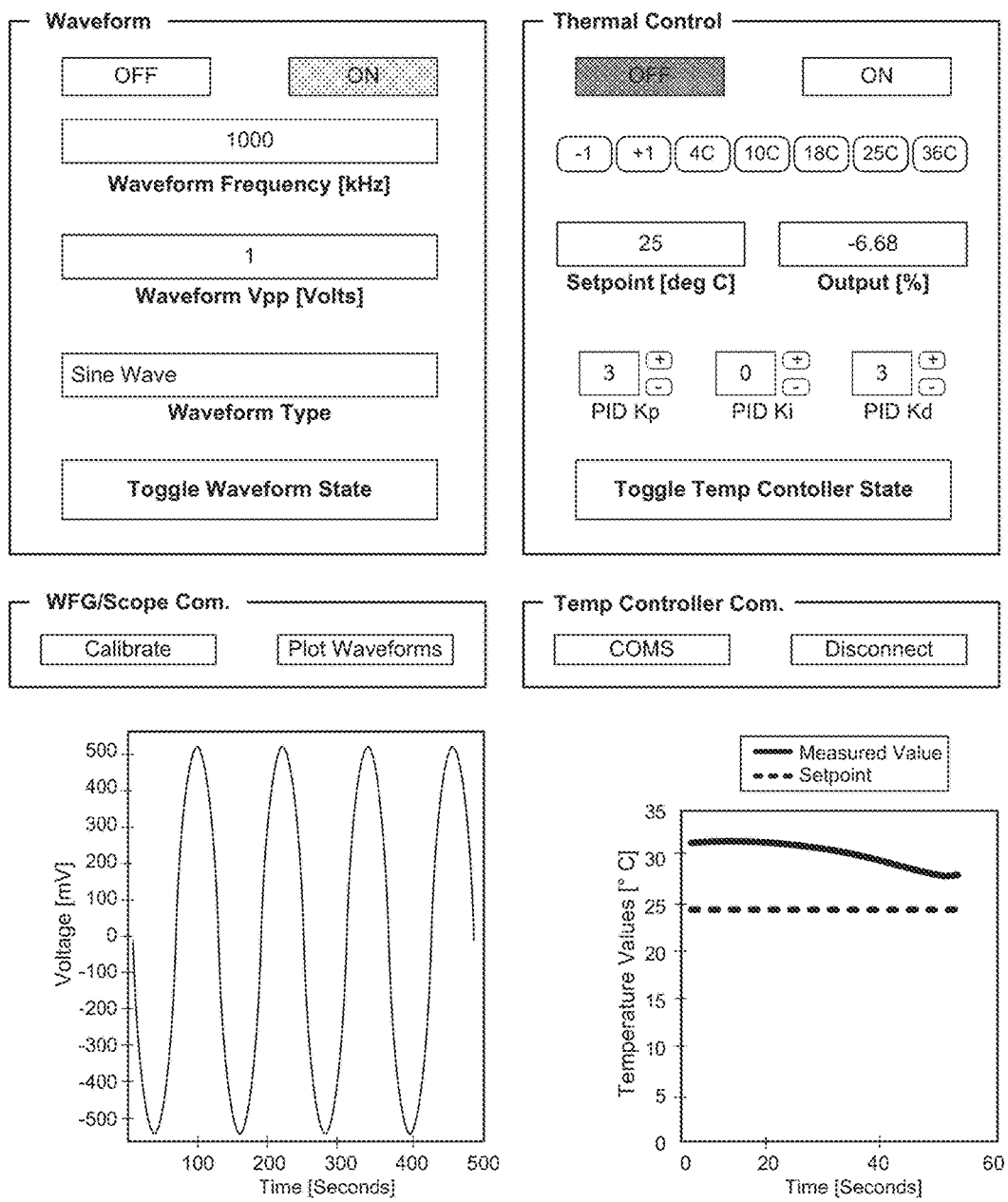
FIG. 3C illustrates an exemplary GUI configured to plot temperature and waveform data according to some embodiments of the invention.

The nest 300 can include a serial port 350 which allows the microprocessor of the controller 308 to communicate with an external master controller 154 via the interface 310. In addition, the microprocessor of the controller 308 can communicate (e.g., via a Plink tool (not shown)) with the electrical signal generation subsystem 304 and thermal control subsystem 306. Thus, via the combination of the controller 308, the interface 310, and the serial port 350, the electrical signal generation subsystem 308 and the thermal control subsystem 306 can communicate with the external master controller 154. In this manner, the master controller 154 can, among other things, assist the electrical signal generation subsystem 308 by performing scaling calculations for output voltage adjustments. A Graphical User Interface (GUI), one example of which is shown in FIG. 3C, provided via a display device 170 coupled to the external master controller 154, can be configured to plot temperature and waveform data obtained from the thermal control subsystem 306 and the electrical signal generation subsystem 308, respectively. Alternatively, or in addition, the GUI can allow for updates to the controller 308, the thermal control subsystem 306, and the electrical signal generation subsystem 304.

As discussed above, system 150 can include an imaging device 194. In some embodiments, the imaging device 194 comprises a light modulating subsystem 404. The light modulating subsystem 404 can include a digital mirror device (DMD) or a microshutter array system (MSA), either of which can be configured to receive light from a light source 402 and transmits a subset of the received light into an optical train of microscope 400. Alternatively, the light modulating subsystem 404 can include a device that produces its own light (and thus dispenses with the need for a light source 402), such as an organic light emitting diode display (OLED), a liquid crystal on silicon (LCOS) device, a ferroelectric liquid crystal on silicon device (FLCOS), or a transmissive liquid crystal display (LCD). The light modulating subsystem 404 can be, for example, a projector. Thus, the light modulating subsystem 404 can be capable of emitting both structured and unstructured light. One example of a suitable light modulating subsystem 404 is the Mosaic™ system from Andor Technologies™. In certain embodiments, imaging module 164 and/or motive module 162 of system 150 can control the light modulating subsystem 404.

In certain embodiments, the imaging device 194 further comprises a microscope 400. In such embodiments, the nest 300 and light modulating subsystem 404 can be individually configured to be mounted on the microscope 400. The microscope 400 can be, for example, a standard research-grade light microscope or fluorescence microscope. Thus, the nest 300 can be configured to be mounted on the stage 410 of the microscope 400 and/or the light modulating subsystem 404 can be configured to mount on a port of microscope 400. In other embodiments, the nest 300 and the light modulating subsystem 404 described herein can be integral components of microscope 400.

In certain embodiments, the microscope 400 can further include one or more detectors 422. In some embodiments, the detector 422 is controlled by the imaging module 164. The detector 422 can include an eye piece, a charge-coupled device (CCD), a camera (e.g., a digital camera), or any combination thereof. If at least two detectors 422 are present, one detector can be, for example, a fast-frame-rate camera while the other detector can be a high sensitivity camera. Furthermore, the microscope 400 can include an optical train configured to receive reflected and/or emitted light from the microfluidic device 360 and focus at least a portion of the reflected and/or emitted light on the one or more detectors 422. The optical train of the microscope can also include different tube lenses (not shown) for the different detectors, such that the final magnification on each detector can be different.

In certain embodiments, imaging device 194 is configured to use at least two light sources. For example, a first light source 402 can be used to produce structured light (e.g., via the light modulating subsystem 404) and a second light source 432 can be used to provide unstructured light. The first light source 402 can produce structured light for optically-actuated electrokinesis and/or fluorescent excitation, and the second light source 432 can be used to provide bright field illumination. In these embodiments, the motive module 162 can be used to control the first light source 404 and the imaging module 164 can be used to control the second light source 432. The optical train of the microscope 400 can be configured to (1) receive structured light from the light modulating subsystem 404 and focus the structured light on at least a first region in a microfluidic device, such as an optically-actuated electrokinetic device, when the device is being held by the support structure 200, and (2) receive reflected and/or emitted light from the microfluidic device and focus at least a portion of such reflected and/or emitted light onto detector 422. The optical train can be further configured to receive unstructured light from a second light source and focus the unstructured light on at least a second region of the microfluidic device, when the device is held by the support structure 300. In certain embodiments, the first and second regions of the microfluidic device can be overlapping regions. For example, the first region can be a subset of the second region.

Figure 3D:
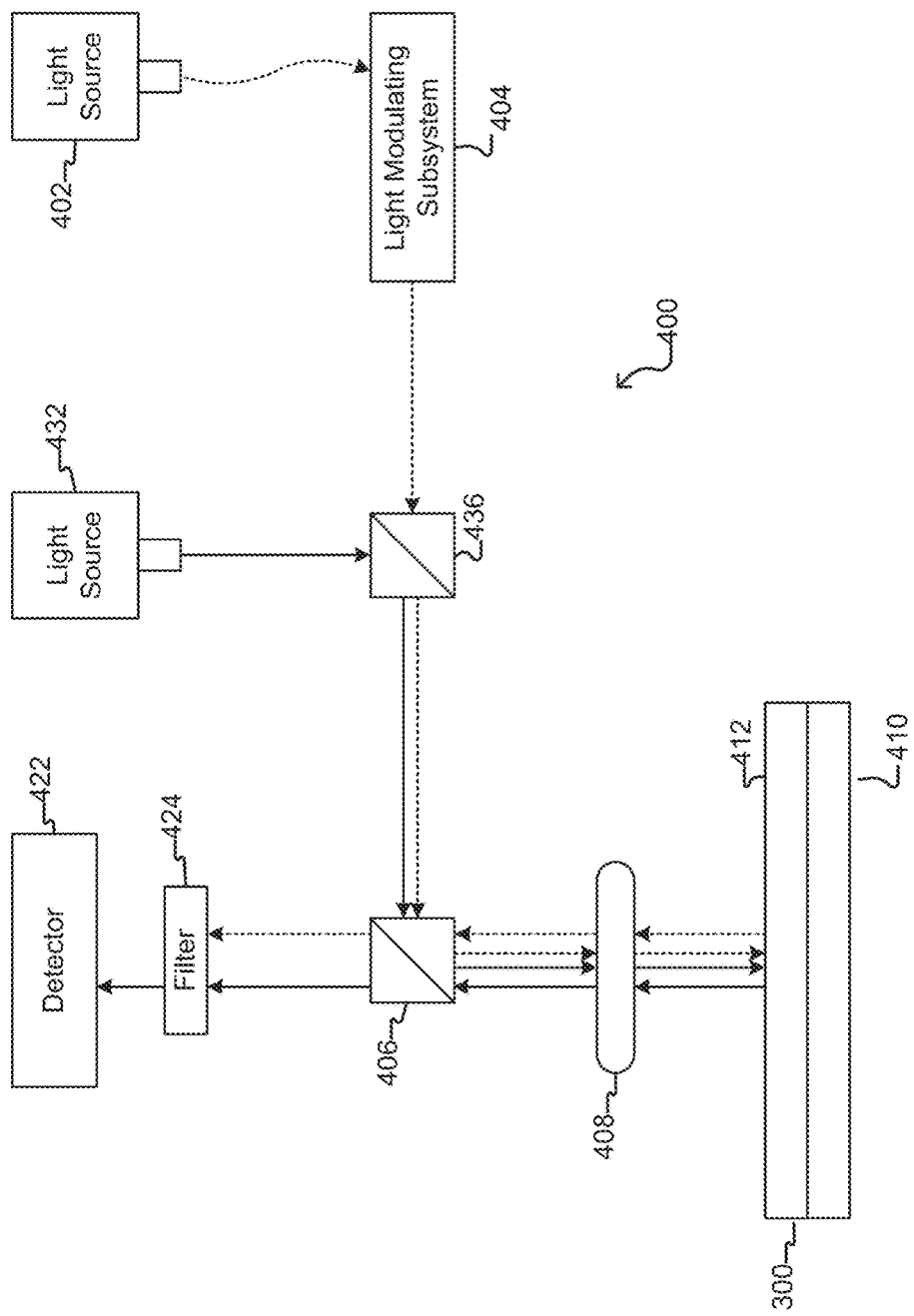
FIG. 3D illustrates an imaging device according to some embodiments of the invention.

In FIG. 3D, the first light source 402 is shown supplying light to a light modulating subsystem 404, which provides structured light to the optical train of the microscope 400. The second light source 432 is shown providing unstructured light to the optical train via a beam splitter 436. Structured light from the light modulating subsystem 404 and unstructured light from the second light source 432 travel from the beam splitter 436 through the optical train together to reach a second beam splitter (or dichroic filter 406, depending on the light provided by the light modulating subsystem 404) where the light gets reflected down through the objective 408 to the sample plane 412. Reflected and/or emitted light from the sample plane 412 then travels back up through the objective 408, through the beam splitter and/or dichroic filter 406, and to another dichroic filter 424. Only a fraction of the light reaching dichroic filter 424 passes through and reaches the detector 422.

In some embodiments, the second light source 432 emits blue light. With an appropriate dichroic filter 424, blue light reflected from the sample plane 412 is able to pass through dichroic filter 424 and reach the detector 422. In contrast, structured light coming from the light modulating subsystem 404 gets reflected from the sample plane 412, but does not pass through the dichroic filter 424. In this example, the dichroic filter 424 is filtering out visible light having a wavelength longer than 495 nm. Such filtering out of the light from the light modulating subsystem 404 would only be complete (as shown) if the light emitted from the light modulating subsystem did not include any wavelengths shorter than 495 nm. In practice, if the light coming from the light modulating subsystem 404 includes wavelengths shorter than 495 nm (e.g., blue wavelengths), then some of the light from the light modulating subsystem would pass through filter 424 to reach the detector 422. In such an embodiment, the filter 424 acts to change the balance between the amount of light that reaches the detector 422 from the first light source 402 and the second light source 432. This can be beneficial if the first light source 402 is significantly stronger than the second light source 432. In other embodiments, the second light source 432 can emit red light, and the dichroic filter 424 can filter out visible light other than red light (e.g., visible light having a wavelength shorter than 650 nm).

Figure 3E:
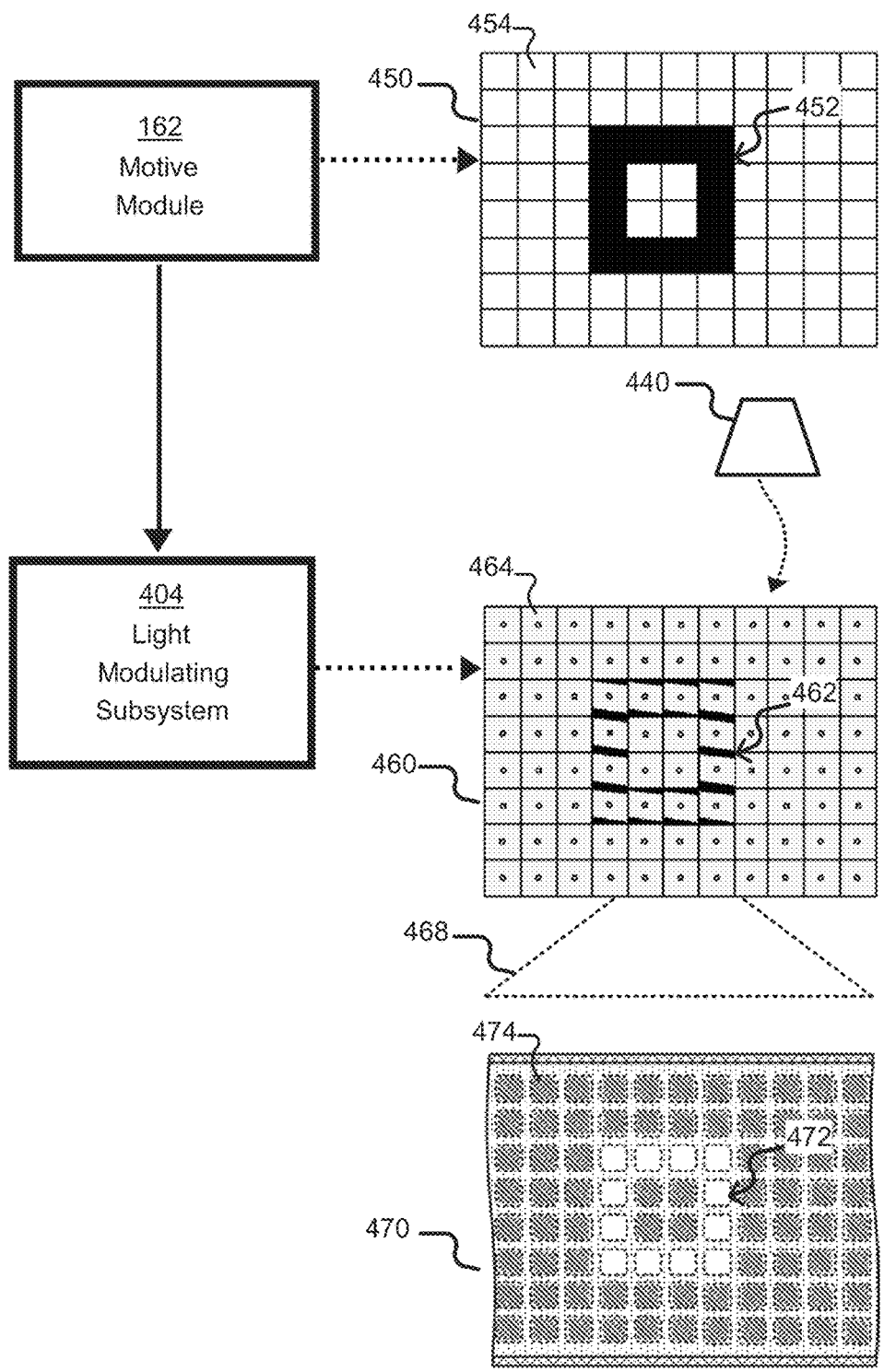
FIG. 3E illustrates communications between a motive module and a light modulating subsystem that control the projection of patterns of light on a microfluidic device, according to a specific embodiment of the invention.

FIG. 3E illustrates communications between the motive module 164 and the light modulating subsystem 404 to project patterns of light on a microfluidic device according to a specific embodiment of the invention. As discussed above with respect to FIG. 3D, the light modulating subsystem 404 may comprise an electrically-addressed spatial light modulator and/or an optically-addressed spatial light modulator. Electrically-addressed spatial light modulators comprise an array of individually-addressable spatial light modulators (i.e. spatial light modulating elements) that are controlled by electrodes. In FIG. 3E, the light modulating subsystem 404 is a Digital Mirror Device (DMD) 460 comprising an array of individually-addressable micro-mirrors 464 that are controlled by an electrodes. However, in other embodiments, the light modulating subsystem 404 can be a Liquid Crystal on Silicon (LCoS) device comprising an array of individually-addressable electrodes that correspond to pixels in a liquid crystal display.

In the embodiment illustrated in FIG. 3E, the light modulating subsystem 404 uses a separate light source 440 to receive and modulate light. However, in other embodiments, the light modulating subsystem 404 comprises its own light source.

As illustrated in FIG. 3E, the motive module 162 transmits information 450 specifying a specific pattern of light ("pattern information") to the light modulating subsystem 404. In some embodiments, the pattern information 450 can comprise a bitmap (or similar pixel-based data structure), vector data, or any combination thereof. For purposes of illustration, the pattern information 450 in FIG. 3E is illustrated as a bitmap comprising an array of pixels 454 and including a square pattern 452 of pixels. Depending on the embodiment, the pattern information 450 can be binary (i.e. specify whether or not to project a pattern of light) or contain values indicating an intensity of light to project. In instances where the spatial light modulators are micro-mirrors 464, the micro-mirrors 464 may create different intensities of light by rapidly switching the mirrors between an "on" and "off" state (i.e. "dithering" the micro-mirrors).

The light modulating subsystem 404 receives the pattern information 450 from the motive module 162 and uses the pattern information 450 to direct the projection of a pattern of light 468 onto DEP electrode regions 474 on the microfluidic device 470. In the embodiment illustrated in FIG. 3E, a DMD 460 rotates a plurality 462 of individually-addressable micro-mirrors 464 corresponding to the square pattern information 450 into an "on state." The square pattern of individual-addressable micro-mirrors 462 modulates the light from the light source 440 to project a pattern of light 468 onto the microfluidic device 470 that illuminates a square pattern of DEP electrode regions 472 in the array of DEP electrode regions 474 in the microfluidic device 470.

In some embodiments, there is a one-to-one correspondence between the array of individually-addressable spatial light modulating elements 464 that project light onto the microfluidic device 470 and the array of DEP electrode regions 474 in the microfluidic device 470. In this way, each individually-addressable spatial light modulating element 464 can project light to generate light-actuated DEP force at a corresponding DEP electrode region 474. In these embodiments, the motive module 162 can send pattern information 450 to the light modulating subsystem 404 that specifies the DEP electrode regions 474 to project light onto. For example, instead of sending bitmap and or vector data to the light modulating subsystem 404, the motive module 162 can communicate directly with the individually-addressable spatial light modulators to control which of the DEP electrode regions 474 are illuminated on the microfluidic device 470. Once illuminated the DEP electrode regions 474 may exert OET or OEW force on surrounding micro-objects.

As discussed above, in some embodiments, the spatial light modulating elements 464 can receive pattern information 450 specifying an intensity of light to project. In a specific embodiment, the pattern information 450 may specify a gradation of light to project over adjacent DEP electrode regions 474 in the microfluidic device. In some embodiments, the pattern information 450 may specify a gradation of light that decreases in intensity over adjacent DEP electrode regions 474. For example, the pattern information 450 may specify that about 100% of the maximum light intensity is to be projected at a first DEP electrode region 474, that 70% of the maximum light intensity is to be projected at a second DEP electrode region 474 adjacent to the first DEP electrode region 474, and that 10% of the maximum light intensity is to be projected at a third DEP electrode region 474 adjacent to the second DEP electrode region 474. Various combinations of light intensities may be used to project a gradation over various numbers of DEP electrode regions 474 (e.g. any decreasing combination of about 100%, about 90%, about 80%, about 70%, about 60%, about 50%, about 40%, about 30%, about 20%, and about 10%, and any values therebetween, of the maximum light intensity over any number of DEP electrode regions 474 and). Similarly, the pattern information 450 may specify a gradation of light that increases in intensity over any number of DEP electrode regions 474 or a gradation of light that both increases and decreases in intensity over any number of DEP electrode regions 474.

In one aspect, the invention provides methods for the automated detection of a micro-object of interest disposed within a microfluidic device. The micro-object of interest can be a cell, such as a mammalian cell (e.g., a blood cell, a hybridoma, a cancer cell, a transformed cell, or the like). Alternatively, the micro-object of interest can be a bead, such as might be used in an assay (e.g., a microbead, a magnetic bead, or the like).

More specifically, the invention provides methods of automatically detecting a micro-object of interest that has similar morphology to features of the microfluidic device. In some instances, detection of micro-objects disposed within a microfluidic device can be complicated by other features of the microfluidic device that have similar morphology to the micro-object of interest. For example, in instances where cells have a diameter of 10 microns, it may be difficult to distinguish the cells from a phototransistor array that is a 10 micron by 10 micro grid. In addition, micro-objects such as cells can be relatively translucent compared to various features of the microfluidic device. Accordingly, it is necessary to identify and remove unwanted features of the microfluidic device (e.g. photo transistor arrays, walls or circuit elements of the microfluidic device) prior to identifying micro-objects of interest.

The invention provides methods of generating differential and filtered images that substantially remove features of the microfluidic device (also referred to herein as "microfluidic device features"), but maintain the micro-objects of interest. In some embodiments, a differential image is used to remove features of the microfluidic device. In these embodiments, a first and second image of the microfluidic device are taken and used to create a differential image. In certain embodiments, the first and second images are digital images. For example, the first and second images can be captured using a digital imaging device, such as a digital camera or a CCD device. Alternatively, the first and second images can be obtained in a non-digitized format and then converted into digital images. After being captured (and digitized, if necessary), the first and second images can be stored in a digital memory device.

In certain instances, actions may be taken to induce movement of the fluid in the microfluidic device after creating the first image and prior to creating the second image. In these instances, inducing movement of the fluid present in the region can involve inducing a small, controlled flow of fluid into or out of the microfluidic device. For example, a pump can be used to introduce a discrete volume of fluid (e.g., 30 pL, 60 pL, 90 pL, or the like) into the flow path of the microfluidic device, thereby causing all of the fluid in the flow path (and any micro-objects contained within the fluid) to shift a small distance (e.g., 2, 5, 10, 15, 20, 30 microns, etc.) in the direction of the fluid flow. Alternatively, a pump can be used to suck a discrete volume of fluid (e.g., 30 pL, 60 pL, 90 pL, etc.) from the flow path of the microfluidic device, thereby causing all of the fluid in the flow path (and any micro-objects contained within the fluid) to shift a small distance (e.g., 2, 5, 10, 15, 20, 30 microns, etc.) in the direction of the fluid flow. In another alternative, the valves that connect the microfluidic device to a source of fluid can be opened. This typically results in a slight movement of fluid within the microfluidic device, causing fluid in the flow path (and any micro-objects contained within the fluid) to shift a small distance. Without intending to be bound by theory, it is believed that this slight movement is caused by a change in surface tension.

In other instances, the position of the microfluidic device is shifted relative to the imaging device 194 after creating the first image and prior to creating the second image. In certain embodiments, shifting the position of the microfluidic device can involve moving a stage that is holding the microfluidic device. The stage can be part of the imaging device 194, such as a conventional microscope (e.g., a light microscope or fluorescence microscope) or a system suitable for operating electrokinetic microfluidic devices. In certain embodiments, the microfluidic device can be shifted by at least 1, 2, 3 microns, or more. Typically, the shift will be in a direction perpendicular to the optical axis of the imaging device 194. For example, if the optical axis corresponds to the z-axis, the shift of the microfluidic device can be in the x,y plane. However, in some embodiments, the shift can include (or even be limited to) movement along the z-axis. In certain embodiments, a piezoelectric device is used to shift the microfluidic device or a stage that is holding the microfluidic device.

After the first image and the second image have been created, various methods can be used to further analyze and process the first and second images. For example, the light intensity value $L_i$ of each pixel $P_i$ (i=1 to n) in the image can be evaluated and/or recorded, where n is the number of pixels in the image. The light intensity value $L_i$ can be the actual observed light intensity value $L_{i,obs}$ for pixel $P_i$. Alternatively, the light intensity values can be smoothed. For example, $L_i$ can be an average of the $L_{i,obs}$ for pixel $P_i$ and some or all of the pixels that contact (i.e., immediately surround) pixel $P_i$. In another alternative, the light intensity value $L_i$ can be the actual observed light intensity value $L_{i,obs}$ for pixel $P_i$ minus a background light intensity value $L_{bkgd}$. In certain embodiments, the light intensity value $L_i$ of each pixel $P_i$ is represented using 0-8 bits, 0-10 bits, 0-12 bits, or 0-14 bits. Using a larger number of bits to represent the light intensity values $L_i$ provides for superior analysis of weak signals.

In some embodiments, the differential image is generated by subtracting the first image from the second image. In other embodiments, the differential image is generated by subtracting the second image from the first image. In some embodiments, a negative light intensity value $L_i$ may be assigned to some or all of the pixels $P_i$ from one of the images and a positive light intensity value $L_i$ may be assigned to some or all of the pixels $P_i$ from the other image. In these embodiments, the light intensity values $L_i$ for the pixels $P_i$ in the two images may be added to subtract one image from the other image. By subtracting the same pixels present in the first image and the second image, static features of the microfluidic device, as opposed to mobile micro-objects of interest, can be removed prior to analyzing the image to identify the micro-objects of interest. For example, the phototransistor array and/or microfluidic circuit elements (e.g. walls) can be removed by creating a differential image that subtracts out pixels that represent such features.

Prior to subtracting one image from the other, the first and second images can be aligned computationally and regions of the first and second images that can't be aligned can optionally be discard. Such alignment can involve the use of one or more identifiable reference points, such as circuit elements within the microfluidic device (e.g. a channel or a sequestration pen within the microfluidic device). The differential image can be generated computationally and then stored in a digital memory device.

After a differential image has been created, various methods can be used to further analyze and process the differential image prior to identifying micro-objects of interest. In certain embodiments, analyzing the differential image further comprises identifying each pixel $P_i$ that has a positive light intensity value $L_i$ as being a positive-value pixel and identifying each pixel $P_i$ that has a negative light intensity value $L_i$ as a negative-value pixel. In other embodiments, analyzing the differential image further comprises: comparing the light intensity value $L_i$ of each pixel $P_i$ to a predetermined threshold light intensity value $L^\circ$; and identifying each pixel $P_i$ having an $L_i$ greater than $L^\circ$ as a positive-value pixel and each pixel $P_i$ having an $L_i$ less than $-1*L^\circ$ as a negative-value pixel. In certain embodiments, $L^\circ$ can be based on the average light intensity value $L_{avg}$ of the set of light intensity values $L_i$ obtained from the set of pixels $P_i$ (i=1 to n). For the calculation of $L_{avg}$, any pixel $P_i$ having a light intensity value $L_i$ that is negative can be multiplied by the factor $-1$ prior to the calculation. Thus, for example, $L^\circ$ can be equal to $L_{avg}$. In certain related embodiments, $L^\circ$ can be based on the average light intensity value $L_{avg}$ and the standard deviation $\sigma$ of the set of light intensity values $L_i$ obtained from the set of pixels $P_i$ (i=1 to n). For example, $L^\circ$ can equal $L_{avg}$ plus some multiple of $\sigma$ (e.g., $L^\circ$ can equal $L_{avg}+1.6\sigma$, $L_{avg}+2.0\sigma$, $L_{avg}+3.0\sigma$, etc.). In certain embodiments, an optimum value for $L^\circ$ is determined empirically.

In alternate embodiments, computational transforms may be used to identify and remove microfluidic device features from one or more images of the microfluidic device. For example, a Fourier transform may be used to identify features of the microfluidic device that are periodic, such as a phototransistor array, periodic circuit elements (e.g. walls) and filter out the periodic features. In a specific embodiment, a Discrete Fourier Transform ("DFT") is applied to an image of the microfluidic device and pixels corresponding to the frequency domain of the DFT are filtered out of the image. After the pixels corresponding to the frequency domain are filtered out, an inverse DFT is applied to produce a filtered image. In embodiments where a filtered image is created, some or all pixels $P_i$ in the image have positive light intensity values $L_i$ and can be processed and/or analyzed as discussed above with the respect to differential images.

In certain embodiments, a single pixel can corresponds to an area in the microfluidic device that is substantially similar to the cross-sectional area of a micro-object of interest. Each pixel can, for example, correspond to an area in the microfluidic device of substantially 5 microns$^2$ (or 4 microns$^2$, 3 microns$^2$, 2 microns$^2$, 1 microns$^2$, etc.) and the cross-sectional area of a micro-object can be substantially 5 microns$^2$ (or 4 microns$^2$, 3 microns$^2$, 2 microns$^2$, 1 microns$^2$, etc.). In such embodiments, a single positive-value (or negative value) pixel can represent the location of a micro-object. Thus, in embodiments that use a differential image to identify micro-objects of interest, pixels identified as positive-value pixels can represent the current location of a micro-object (i.e., the position after movement of the fluid), and pixels identified as negative-value pixels can represent the former location of a micro-object (i.e., the position before movement of the fluid). However, if the differential image is generated by subtracting the second image from the first image, then pixels identified as positive-value pixels can represent the former location of a micro-object and pixels identified as negative-value pixels can represent the current location of the micro-object.

In other embodiments, a single pixel can correspond to an area in the microfluidic device that is substantially smaller than the cross-sectional area of a micro-object of interest. For example, the micro-object may have a cross-sectional area of about 80 microns$^2$, whereas a pixel may correspond to an area of about 2 microns$^2$. In such embodiments, one or more clusters of pixels will be required to cover the cross-sectional area of the micro-object (e.g., in the foregoing example, it would take substantially 40 pixels to cover the cross-section area of the micro-object, or 24 pixels to cover the cross-sectional area of the circumference of the micro-object). Accordingly, in certain embodiments, analyzing the differential and/or filtered image further comprises determining whether a set of positive-value (or negative-value) pixels form one or more clusters of pixels (i.e. pixel clusters) aggregated proximal to each other and whether the area represented by the set of pixel cluster(s) is sufficiently large in comparison to the micro-object being detected. For example, a set of pixel clusters that correspond to an area that is at least 50% of (or 60%, 70%, 80%, 90%, or substantially similar to) the cross-sectional area of a micro-object of interest can be identified as representing the location of the micro-object. Alternatively, a set of pixel clusters that correspond to an area that is at least 70% of (or 80%, 90%, or substantially similar to) the cross-sectional circumference of a micro-object of interest can be identified as representing the location of the micro-object. In instances, where the images include multiple micro-objects, multiple sets of pixel clusters can be identified and analyzed to determine whether each set of pixel clusters corresponds to a micro-object of interest.

The analysis of a set of pixel clusters can further comprise a number of other features aside from the area and circumference of the pixel clusters. The set of pixel clusters may be analyzed according to global morphology (i.e. the size and shape of the set of one or more pixel clusters), local morphology (i.e. the size and shape of the individual pixel clusters), positive and negative light intensity values $L_i$, and other features based on a combination of these elements (e.g. light intensity as a function of size). Various methods may be used to analyze the set of pixel clusters including traditional machine learning techniques where the above-discussed features are computed for a set of images of micro-objects and used to train a classifier to identify micro-objects of interest in new images based on the same features.

In certain embodiments, the differential image can be analyzed for pairs of positive-value and negative-value pixels (or sets of pixel clusters), and the identification of a micro-object can be limited to instances in which the differential image contains corresponding positive-value and a negative-value pixel (or sets of pixel clusters). In certain related embodiments, the identification of a micro-object can be limited to instances in which the differential image contains a pair of positive-value and negative-value pixels (or sets of pixel clusters) and the difference in the relative positions of the positive-value and negative-value pixels (or sets of pixel clusters) is consistent with the magnitude of movement of fluid induced in the region.

In addition to information specifying whether a micro-object is present, micro-object identification can provide various additional information. As discussed above, the differential and/or filtered image may be analyzed with respect to the size and shape of the potential micro-object. In doing so, various information regarding the micro-object may be produced including the radius of the micro-object, the perimeter of the micro-object and a centroid associated with the micro-object.

Once the micro-objects have been identified, various operations can be performed on the micro-objects. In some embodiments, the cell identification will be used to count micro-objects in the microfluidic circuit. In some embodiments, the identified micro-objects will be associated with various circuit elements of the microfluidic circuit (e.g. channel, a sequestration pen, a trap, or any combination thereof) and/or spatial locations on the microfluidic circuit. In these embodiments, the density of micro-objects in a specific area of the microfluidic circuit (e.g. a channel, a sequestration pen, a trap, or any combination thereof) may be calculated.

Micro-object identification may also be used in conjunction with manipulating or repositioning the micro-objects using force, such as OET or DEP force. In some embodiments, micro-objects that are identified in a specific circuit element (e.g. channel or sequestration pen) or location of the microfluidic circuit may be moved to (i.e. repositioned in) another type of circuit element or location of the microfluidic circuit. For example, micro-objects may be identified in a channel in the microfluidic circuit and repositioned in sequestration pens in the microfluidic circuit (referred to herein as "penning" a micro-object). Conversely, micro-objects identified in sequestration pens in the microfluidic circuit may be moved to in channels in the microfluidic circuit. Alternately, one or more micro-objects may identified in one sequestration pen and repositioned in an empty sequestration pen (referred to herein as "re-penning" a micro-object). According to the embodiment, the micro-objects may be moved using various mechanisms, including OET and DEP force. Similarly, micro-objects may be repositioned sequentially (i.e. one micro-object at a time), in parallel, or any combination thereof (e.g. sequentially repositioning groups of multiple cells in parallel).

In instances where micro-objects are repositioned from the channel to individual sequestration pens (or re-penning from an individual sequestration pen to another sequestration pen), different algorithms may be used to assign micro-objects to empty sequestration pens. In some embodiments, an algorithm will be used to assign micro-objects to empty sequestration pens such that distance between the micro-objects and the pens (i.e. the trajectory or path that the micro-objects have to travel during repositioning) is minimized. In these embodiments, the use of force (e.g. OET or DEP force) to move the micro-objects is also minimized because the micro-objects are only required to travel a minimum distance to be repositioned in an empty sequestration pen.

In these embodiments, a local micro-object density in a channel (i.e. number of micro-objects within a specific spatial area of the channel) may be used to determine a suitable algorithm to assign specific micro-objects in the channel to empty sequestration pens. Local micro-object density may be computed in a number of ways. In some embodiments, local micro-object density may be computed based on a fixed size area (e.g. 200 microns$^2$, or an area of the channel 100 microns long and extending the width of the channel) or using approaches that use various sizes of areas. In other embodiments, local micro-object density may calculated based on clusters of identified micro-objects or the distance between identified micro-objects. Local micro-object density also may be computed by subdividing the channel into a grid or using a "sliding window" approach to compute density for overlapping areas of the channel.

If the local micro-object density is above a threshold value $T1_{density}$, then micro-objects may be assigned to the nearest empty sequestration pens such that the distance between the micro-objects and sequestration pens is minimized. If the local micro-object density is below a specific threshold value $T1_{density}$, then the empty sequestration pens may be assigned to the micro-objects that are closest to the empty sequestration pens, such that the distance between the micro-objects and the sequestration pens is minimized. In some instances, local $T1_{density}$, may be computed based on the number of empty pens as well as the density of micro-objects within the channel in a predefined neighborhood area.

Different methods of computing the distance between a micro-object and an empty sequestration pen (i.e. the trajectory the micro-object or path needs to be moved during penning) may be used to assign specific micro-objects to empty sequestration pens. In some embodiments, the distance between the micro-object and a potential sequestration pen may be computed based only on the optimal trajectory using OET and/or DEP force. In some instances, the optimal trajectory using OET or DEP force involves a combination of orthogonal motion paths (e.g. combination of distinct movement only along a y-axis and an x-axis) to move the micro-objects. In other instances, the distance may be based on the shortest possible path between the micro-object and the sequestration pen, without constraint (i.e. the micro-objects may travel along any path to reach the sequestration pens). In most embodiments, the micro-objects will be re-positioned (i.e. "penned" or "re-penned") using the same trajectory as determined by the algorithm used to calculate the distance (trajectory).

Similarly, in instances where a large number of micro-objects are assigned to sequestration pens (or vice versa), different algorithms may be used to compute the optimal assignment of micro-objects to pens (or vice versa). These algorithms can use different computational methods of determining a micro-object-to-sequestration pen assignment that minimizes the overall distance (i.e. length of the trajectory) that the micro-objects need to be moved in order to reposition the micro-objects into sequestration pens. For example, the algorithms may use the sum of the lengths of all the trajectories as a heuristic to minimize the distance that the micro-objects need to travel. In some embodiments, constraints such as a maximum distance that a micro-object can be moved during repositioning may be introduced into the computation of the optimal assignment. Various combinatorial algorithms may be used to compute the optimal assignment between micro-objects and sequestration pens. Suitable algorithms include: greedy algorithms, nonlinear optimization, heuristic-based algorithms and constrained search. Other similar algorithms are known in the art.

Once the optimal assignment and trajectory has been computed for the micro-objects, a force, such as OET and/or DEP, may be used to move the micro-objects to their assigned pens. The micro-objects may be repositioned using patterns of light, such as a "light cage", that surround the micro-objects and subject the micro-objects to OET and/or DEP force or by using bars or similar structures to apply OET and/or DEP force to the micro-objects. Typically, a light cage will be a structure that substantially encloses the micro-object (e.g. a square, a circle or a polygon). However, in some instances, a light cage may contain a break or an opening such that the micro-object is not fully enclosed.

As discussed above, in most embodiments, the micro-objects will be moved according to the distance (trajectory) used to compute the optimal assignment of micro-objects to pens. According to the embodiment, micro-objects may be moved sequentially or in parallel any combination thereof (e.g. sequentially moving groups of cells in parallel). In embodiments where the micro-objects are moved in parallel, the algorithm used to compute the optimal assignment or trajectory may compare the trajectories and ensure that the micro-objects do not collide when they are moved in parallel by modifying the trajectory and assignments of the micro-objects to pens. In a specific embodiment, the algorithm may "swap" micro-object assignments to pens when a potential collision is identified. In this embodiment, when the optimal trajectory for a first micro-objects intersects with the optimal trajectory for a second micro-objects, the optimal trajectory for the first micro-object is assigned to the second micro-object and the optimal trajectory for the second micro-object is assigned to the first micro-object. In another specific embodiment, the algorithm delays the repositioning of the first micro-object until such a time that the first and second micro-objects can move along their respective trajectories without colliding.

In some instances, the micro-object density may be so high that the micro-objects need to be separated from one another prior to assigning the micro-objects to sequestration pens and repositioning (i.e. "penning" or "re-penning") the micro-objects. For example, the micro-object density may be so high that the micro-objects cannot be penned using OET and/or DEP force because the light cage used to reposition objects using OET and/or DEP force cannot be used on a single micro-object without interfering with other micro-objects. This interference is of particular concern in instances where it is important to minimize the amount of OET and/or DEP force applied to the micro-object. For examples, instances where the micro-objects could be harmed by OET and/or DEP force or by-products of OET force (e.g. electrolysis associated with OET and/or DEP force). In these instances, information produced during micro-object identification (e.g. the radius, the centroid, the perimeter and the location of a micro-object) may be used to move the micro-objects such the micro-objects may be penned or re-penned without interfering with other cells (herein referred to as "separating" the micro-objects).

In order to identify instances where the micro-objects need to be separated prior to penning, a local micro-object density may be computed based on a defined spatial region and compared to a second threshold value $T2_{density}$. Alternately, the distance between the micro-objects may be computed (e.g. the distance between centroids of micro-objects, the distance between the perimeters of the micro-objects) and used to determine whether the micro-objects need to be separated. However, as can appreciated, in some instances, the distance between micro-objects may be too small to identify the micro-objects as separate micro-objects and micro-objects. In these instances, the micro-objects may be re-identified after repositioning (i.e. "penning") the micro-objects to ensure that each sequestration pen contains a single micro-object.

In some embodiments, a modified light box is used to separate the micro-objects prior to, or during, penning (or re-penning). In these embodiments, a division algorithm is used to compute a set of vertices that partition each identified micro-object in the spatial region of the microfluidic device (e.g. the portion of the channel or the sequestration pen) from the other micro-objects in the same spatial region. However, as can be appreciated by those skilled in the art, the set of vertices may be drawn such that only a subset of the micro-objects in the spatial region of the microfluidic device are separated from the other micro-objects. For example, the set of vertices may only separate the subset of micro-objects in the spatial region that need to be repositioned due to their close proximity to other micro-objects.

In a specific embodiment, a Delaunay triangulation is computed using the centroids of each micro-object. The Delaunay triangulation produces a set of triangles that connect the centroids of the micro-objects. A Voronoi diagram is then computed based on the circumcircles of the triangles computed using the Delaunay Triangulation. The Voronoi diagram is a set of vertices that divide the spatial area into a sub-areas such that the distance between the set of vertices and the centroid of the micro-object is maximized. Other methods of computing a set of vertices that partition each cell from the other cells in the spatial region are known in the art.

Once the set of vertices has been computed, the set of vertices can be used in combination with OET and/or DEP forces to move the micro-objects. In one embodiment, one or more "modified light cages" are generated using the intersection of set of the vertices and the light cage shape typically used to move a micro-object (e.g. a square or circle). Because the intersection of the vertices and the light cages defines an area where the light cages do not intersect or overlap, the light cage can be re-drawn as a modified light cage surrounding the intersection (or a subset of the intersection) such that the modified light cage does not interfere with other micro-objects. The modified light cages can then be used to separate micro-objects by repositioning the micro-object by moving the micro-objects away from each other. In some instances, modified light cage may be re-drawn as the micro-objects are repositioned such that the original light cages are drawn when the micro-objects are in the final position.

Modified light cages may be used to reposition the micro-objects in a variety of embodiments. Depending on the embodiment, the modified light cages for two proximate micro-objects are used to reposition the micro-objects prior to, or after, computing and selecting the trajectory and assignment to a sequestration pen for each micro-object. In some embodiments, modified light cages are used to reposition micro-objects iteratively or sequentially. In addition, modified light cages may be used to pen micro-objects in their assigned sequestration pens. In some embodiments, micro-objects that are closest to the perimeter of the spatial area or closest together in space may be re-positioned or penned prior to repositioning or penning other micro-objects.

In moving the micro-objects, the speed at which OET and/or DEP is used to move the cells may be gradually accelerated in order to "ramp up" motion of the micro-objects and ensure that the micro-objects are not lost from their light cages. For example, in a specific embodiment, the initial velocity of the micro-objects may be gradually accelerated from a low initial velocity to a higher travelling velocity. This gradual acceleration may be applied both in instances where the micro-objects are automatically repositioned (e.g. penning, re-penning and export) and in instances where the micro-objects are manually repositioned (e.g. manually selecting and moving a cell). Similarly, the high travelling velocity may be "ramped down" to a final velocity of zero when the micro-objects reach the end of their trajectory and are at their final position.

Figure 4A:
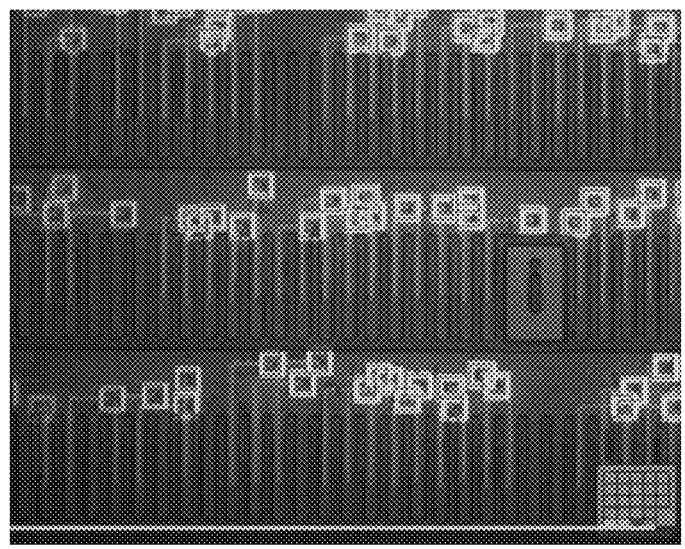
FIGS. 4A, 4B, and 4C depict the penning of micro-objects in parallel, according to one embodiment of the invention.
Figure 4B:
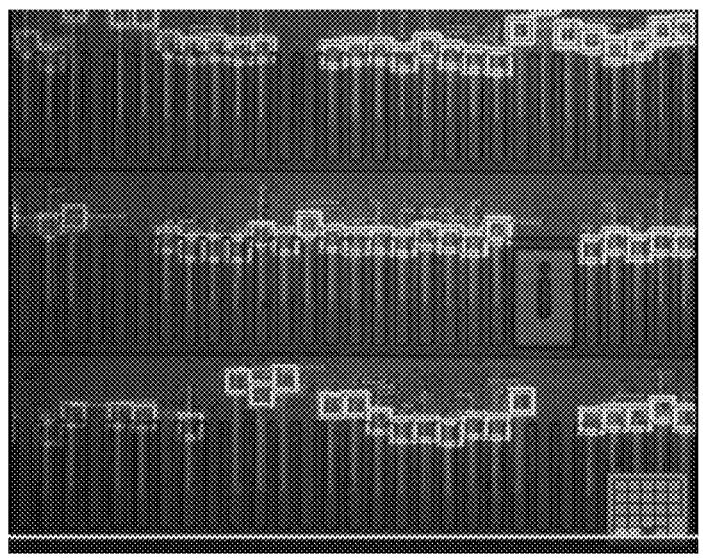
Figure 4C:
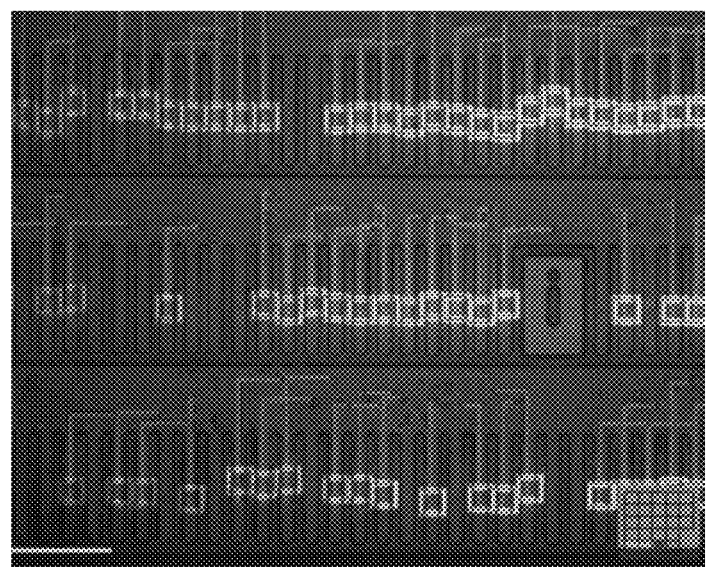

FIGS. 4A, 4B, and 4C illustrate micro-object identification and penning according to one embodiment of the invention. In FIG. 4A, biological cells within the channel of a microfluidic circuit are shown immediately following the identification of the cells and the assignment of cells to pens. The black boxes surrounding the cells illustrate the output of the cell identification algorithm—that is, an identification of cells indicated by a box around the cell. The white boxes surrounding the black boxes are the light cages of OET force used to reposition the cells. Lastly, the black lines that connect the boxes surrounding the cells to the sequestration pens illustrate the optimal trajectory computed in assigning the cells to sequestration pens. FIG. 4B shows the same cells at a later time point in which the light cages have been moved along their selected trajectories. FIG. 4C shows the same cells at a third time point where the light cages have been almost fully moved along their selected trajectories to position the cells in the sequestration pens.

Figure 5A:
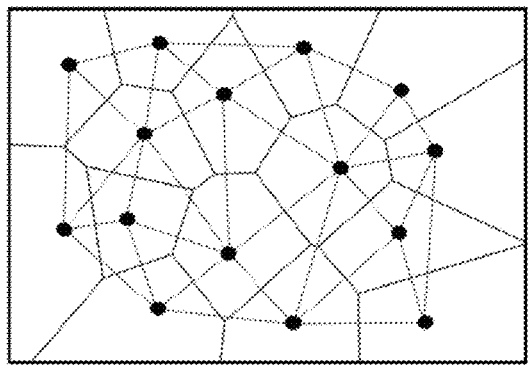
FIGS. 5A-5F illustrate the generation of modified light cages that can be used to separate micro-objects, according to a specific embodiment of the present invention.
Figure 5B:
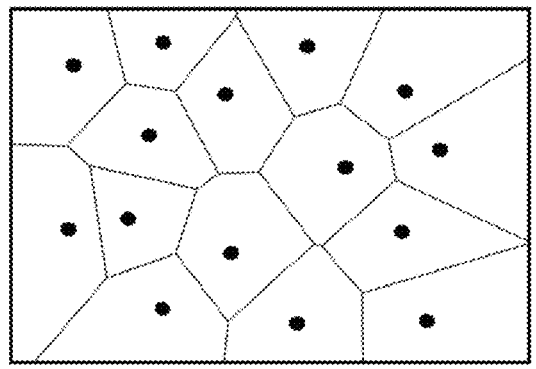
Figure 5C:
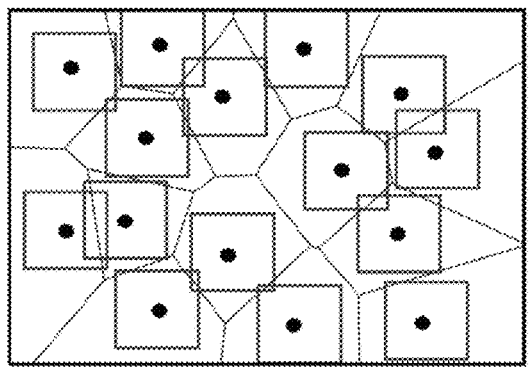
Figure 5D:
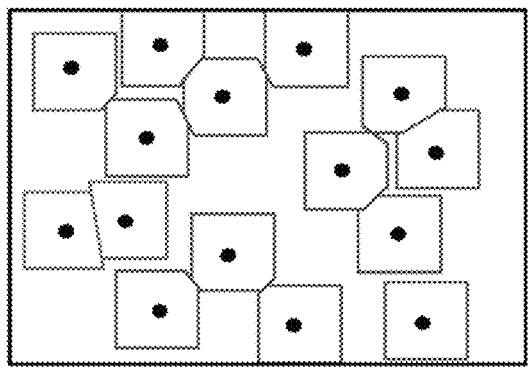
Figure 5E:
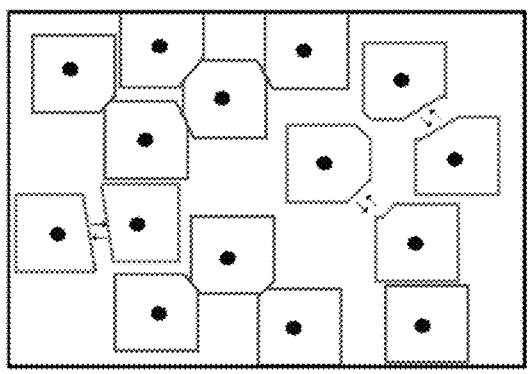
Figure 5F:
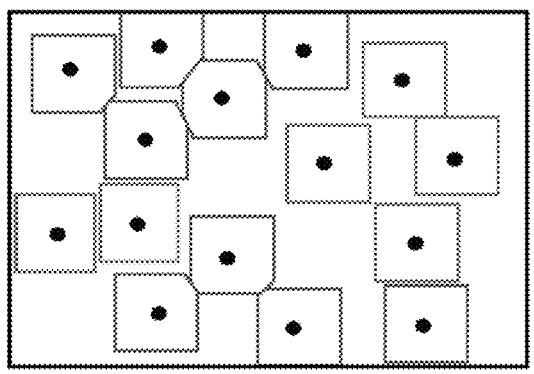

FIGS. 5A-5F illustrate micro-object separation according to a specific embodiment of the present invention. FIG. 5A illustrates the Delauney triangulation of a set of micro-objects within a specified spatial region and the corresponding Voronoi diagram. FIG. 5B illustrates the corresponding Voronoi diagram without the Delauney triangulation. FIG. 5C illustrates light cages typically used to move micro-objects overlaid upon the Voronoi diagram. FIG. 5D illustrates modified light cages generated by computing the intersection between the typical light cages of FIG. 5C and the Voronoi diagram. FIG. 5E illustrates the separation of the micro-objects that are in close proximity with each other using the modified light cages. FIG. 5F illustrates the separated micro-objects.

The methods of the invention are useful for the automated detection of micro-objects in all types of microfluidic devices. In certain embodiments, the microfluidic device can include a flow region (or flow channel) and one or more chambers (or sequestration pens). Alternatively, or in addition, the microfluidic device can be an electrokinetic device, such as an optically actuated electrokinetic device, or can include a region configured for electrokinesis. Electrokinetic devices, particularly electrokinetic devices having an array of transistors (e.g., phototransistors), can provide a particularly complicated background if the transistors in the array have an area that is similar to the cross-sectional area of a micro-object that is being detected. The methods described herein can be particularly effective at detecting micro-objects disposed in such a device.

In certain embodiments, the invention further provides machine readable storage devices for storing non-transitory machine readable instructions for carrying out any of the methods described herein. The machine readable instructions can control the imaging device used to obtain the images and/or a processor (e.g., in a computational device) that aligns the images, generates differential images, and/or analyzes the differential images.

Although specific embodiments and applications of the invention have been described in this specification, these embodiments and applications are exemplary only, and many variations are possible.

What is claimed:

1. A method of re-positioning micro-objects in a microfluidic device, the method comprising:
    identifying a set of micro-objects disposed within a specified spatial region of the microfluidic device;
    calculating a set of vertices that divide the specified spatial region into sub-regions, each of which contains one or more micro-object(s) of the set of micro-objects;
    generating a modified first light cage for at least one micro-object of the set of micro-objects based on the calculated set of vertices; and
    moving the modified first light cage relative to the specified spatial region of the microfluidic device to re-position the at least one micro-object.

2. The method of claim 1, wherein calculating said set of vertices that divide the specified spatial region into sub-regions comprises calculating a set of vertices that maximize the distance between a subset of the calculated set of vertices that are adjacent to each micro-object of the set of micro-objects and the micro-object.

3. The method of claim 1, wherein calculating said set of vertices comprises calculating a set of vertices that divide the specified spatial region into sub-regions, wherein at least a subset of the sub-regions contains a single micro-object of the set of micro-objects.

4. The method of claim 3, wherein calculating the set of vertices comprises:
    calculating a Delaunay triangulation of the set of micro-objects;
    generating a Voronoi diagram based on the Delaunay triangulation of the set of micro-objects; and
    identifying the set of vertices based on the Voronoi diagram.

5. The method of claim 1, wherein generating the modified first light cage comprises:
    computing, for a first micro-object of the set of micro-objects, a first light cage;
    computing an intersection between the first light cage and the set of vertices; and
    generating the modified first light cage based on the intersection between the first light cage and the set of vertices.

6. The method of claim 5, further comprising:
    computing, for a second micro-object of the set of micro-objects, a second light cage;
    computing the intersection between the second light cage and the set of vertices; and
    generating a modified second light cage based on the intersection between the second light cage and the set of vertices, wherein the modified second light cage does not intersect with the modified first light cage.

7. The method of claim 6, further comprising moving both the modified first light cage and the modified second light cage relative to the specified spatial region of the microfluidic device to physically separate the first micro-object and the second micro-object.

8. The method of claim 7, wherein the first micro-object and the second micro-object are initially located in adjacent sub-regions of the specified spatial region.

9. The method of claim 1, wherein the at least one micro-object is re-positioned from a first location in the microfluidic device to a second location.

10. The method of claim 9, wherein the first location is within a microfluidic channel of the microfluidic device and the second location is within a sequestration pen of the microfluidic device.

11. The method of claim 10, wherein the sequestration pen comprises an isolation region and a connection region which connects the isolation region to the microfluidic channel.

12. The method of claim 11, wherein the modified first light cage moves the at least one micro-object from the microfluidic channel, through the connection region, and into in the isolation region of the sequestration pen.

13. The method of claim 9, wherein the first location is within a sequestration pen of the microfluidic device and the second location is within a microfluidic channel of the microfluidic device.

14. The method of claim 9, wherein the first location is within a first sequestration pen of the microfluidic device and the second location is within a second sequestration pen of the microfluidic device.

15. The method of claim 1, wherein re-positioning the at least one micro-object of the set of micro-objects comprises accelerating each of the at least one micro-objects from an initial velocity to a traveling velocity over a first time period.

16. The method of claim 15, wherein re-positioning the at least one micro-object of the set of micro-objects comprises decelerating each of the at least one micro-objects from the traveling velocity to a final velocity over a second time period.

17. The method of claim 1, wherein identifying the set of micro-objects comprises using machine learning techniques.

18. The method of claim 1, wherein the at least one micro-object is a cell.

19. The method of claim 18, wherein the cell is a mammalian cell.

20. The method of claim 1, wherein the microfluidic device comprises a dielectrophoresis (DEP) configuration.

21. The method of claim 20, wherein the modified first light cage activates DEP electrodes in the microfluidic device, thereby generating DEP forces that move the at least one micro-object.

22. A method of re-positioning a micro-object in a microfluidic device, the method comprising:
    identifying a set of micro-objects disposed within a specified spatial region of the microfluidic device;
    generating a modified first light cage to encompass at least one micro-object of the set of micro-objects; and
    moving the modified light cage to re-position the at least one micro-object and separate it the at least one micro-object from the set of micro-objects.

23. The method of claim 22, wherein the at least one micro-object is re-positioned from a first location in the microfluidic device to a second location.

24. The method of claim 23, wherein the first location is within a microfluidic channel of the microfluidic device and the second location is within a sequestration pen of the microfluidic device.

25. The method of claim 24, wherein the sequestration pen comprises an isolation region and a connection region which connects the isolation region to the microfluidic channel.

26. The method of claim 25, wherein the modified first light cage moves the at least one micro-object from the microfluidic channel, through the connection region, and into in the isolation region of the sequestration pen.

27. The method of claim 23, wherein the first location is within a sequestration pen of the microfluidic device and the second location is within a microfluidic channel of the microfluidic device.

28. The method of claim 23, wherein the first location is within a first sequestration pen of the microfluidic device and the second location is within a second sequestration pen of the microfluidic device.

29. The method of claim 22, wherein re-positioning the at least one micro-object of the set of micro-objects comprises accelerating each of the at least one micro-objects from an initial velocity to a traveling velocity over a first time period.

30. The method of claim 29, wherein re-positioning the at least one micro-object of the set of micro-objects comprises decelerating each of the at least one micro-objects from the traveling velocity to a final velocity over a second time period.

31. The method of claim 22, wherein identifying the set of micro-objects comprises using machine learning techniques.

32. The method of claim 22, wherein the at least one micro-object is a cell.

33. The method of claim 32, wherein the cell is a mammalian cell.

34. The method of claim 22, wherein the microfluidic device comprises a dielectrophoresis (DEP) configuration.

35. The method of claim 34, wherein the modified first light cage activates DEP electrodes in the microfluidic device, thereby generating DEP forces that move the at least one micro-object.

* * * * *

UNITED STATES PATENT AND TRADEMARK OFFICE
CERTIFICATE OF CORRECTION

PATENT NO. : 9,996,920 B2  
APPLICATION NO. : 14/963230  
DATED : June 12, 2018  
INVENTOR(S) : Fenglei Du et al.

Page 1 of 1

It is certified that error appears in the above-identified patent and that said Letters Patent is hereby corrected as shown below:

In the Claims

In Column 43, Line 30, Claim 1 please delete "micro-object(s)" and replace with --micro-objects--.
In Column 43, Line 42, Claim 2 please insert --at least one-- before "micro-object".
In Column 44, Line 40, Claim 15 please delete "each of".
In Column 44, Line 40, Claim 15 please delete "micro-objects" and replace with --micro-object--.
In Column 44, Line 44, Claim 16 please delete "each of".
In Column 44, Line 44, Claim 16 please delete "micro-objects" and replace with --micro-object--.
In Column 44, Line 66, Claim 22 please delete "it".
In Column 46, Line 3, Claim 29 please delete "each of".
In Column 46, Line 3, Claim 29 please delete "micro-objects" and replace with --micro-object--.
In Column 46, Line 7, Claim 30 please delete "each of".
In Column 46, Line 7, Claim 30 please delete "micro-objects" and replace with --micro-object--.

Signed and Sealed this  
Sixth Day of November, 2018

Andrei Iancu  
*Director of the United States Patent and Trademark Office*